US012703708B2

(12) United States Patent
Ma et al.

(10) Patent No.: US 12,703,708 B2
(45) Date of Patent: Aug. 11, 2026

(54) MODULATORS OF FPR1 AND METHODS OF USING THE SAME

(71) Applicant: BIOFRONT THERAPEUTICS (BEIJING) CO., LTD., Beijing (CN)

(72) Inventors: Tianwei Ma, Beijing (CN); Zheng Huang, Beijing (CN); Feng Shi, Beijing (CN)

(73) Assignee: BIOFRONT THERAPEUTICS (BEIJING) CO., LTD., Beijing (CN)

(*) Notice: Subject to any disclaimer, the term of this patent is extended or adjusted under 35 U.S.C. 154(b) by 390 days.

(21) Appl. No.: 18/262,034

(22) PCT Filed: Jan. 21, 2021

(86) PCT No.: PCT/CN2021/073155

§ 371 (c)(1), (2) Date: Jul. 19, 2023

(87) PCT Pub. No.: WO2022/155860

PCT Pub. Date: Jul. 28, 2022

(65) Prior Publication Data

US 2024/0300973 A1 Sep. 12, 2024

(51) Int. Cl.

| | |
|---|---|
| ***C07D 498/04*** | (2006.01) |
| ***A61K 31/4162*** | (2006.01) |
| ***A61P 25/28*** | (2006.01) |

(52) U.S. Cl.

CPC ........ *C07D 498/04* (2013.01); *A61K 31/4162* (2013.01); *A61P 25/28* (2018.01)

(58) Field of Classification Search

CPC ..... C07D 498/04; A61K 31/4162; A61P 3/10; A61P 7/02; A61P 9/00; A61P 9/10; A61P 21/00; A61P 25/00; A61P 25/04; A61P 25/08; A61P 25/16; A61P 25/28; A61P 35/00

See application file for complete search history.

(56) References Cited

U.S. PATENT DOCUMENTS

| | | | |
|---|---|---|---|
| 4,938,949 | A | 7/1990 | Borch et al. |
| 2019/0270704 | A1 | 9/2019 | Shirude et al. |

FOREIGN PATENT DOCUMENTS

| | | | | |
|---|---|---|---|---|
| CN | 104080787 | A | 10/2014 | |
| CN | 109715602 | A | 5/2019 | |
| CN | 110724154 | A * | 1/2020 | ........... C07D 498/04 |
| CN | 110997661 | A | 4/2020 | |
| CN | 111868052 | A | 10/2020 | |
| JP | 2019517997 | A | 6/2019 | |
| JP | 2020523330 | A | 8/2020 | |
| WO | WO 2012046030 | A2 | 4/2012 | |
| WO | WO 2013075083 | | 5/2013 | |
| WO | WO 2013075084 | | 5/2013 | |
| WO | WO 2013078320 | | 5/2013 | |
| WO | WO 2013120104 | | 8/2013 | |
| WO | WO 2014124418 | | 8/2014 | |
| WO | WO 2014151142 | | 9/2014 | |
| WO | WO 2015023915 | | 2/2015 | |
| WO | 2019173182 | A1 | 9/2019 | |
| WO | 2020112583 | A1 | 6/2020 | |

OTHER PUBLICATIONS

Tortorella et al., J. Chem Inf. & Model., vol. 56, pp. 1216-1227, publ. Jun. 7, 2016 (Year: 2016).*

Chemcats, RN 1040706-32-8, abstract published by CAS Aug. 13, 2008 (Year: 2008).*

Chemcats, RN 672276-69-6, CAS abstract published Apr. 7, 2004 (Year: 2004).*

Extended European Search Report of European Patent Application No. 21920262.9, dated Oct. 4, 2024.

S. Berge et al., Pharmaceutical Salts, *Journal of Pharmaceutical Sciences*, vol. 66, No. 1, pp. 1-19 (1977).

A. Lauer et al., Anticoagulation with the Oral Direct Thrombin Inhibitor Dabigatran Does Not Enlarge Hematoma Volume in Experimental Intracerebral Hemorrhage, *Circulation*, 124(15), pp. 1654-1662 (2011).

M. Rynkowski et al., A mouse model of intracerebral hemorrhage using autologous blood infusion, *Nature Protocols*, 3(1), pp. 122-128 (2008).

M. Li et al., Astrocyte-derived interleukin-15 exacerbates ischemic brain injury via propagation of cellular immunity, *Proceedings of the National Academy of Sciences*, 114(3), E396-E405 (2016).

O. Bobrovskaya et al., Synthesis and Biological Activity of 3,4-Diaryl-5-[4-(acetylsulfamoyl)phenyl]-4,5-dihydropyrrolo[3,4-c]pyrazol-6(2H)-ones and Their Sodium Salts, *Russian Journal of General Chemistry*, 87(12), pp. 2776-2782 (2017).

International Search Report and Written Opinion in counterpart PCT Application No. PCT/CN2021/073155, mailed Oct. 19, 2021.

* cited by examiner

*Primary Examiner* — Sarah Pihonak

(74) *Attorney, Agent, or Firm* — FINNEGAN, HENDERSON, FARABOW, GARRETT & DUNNER LLP

(57) ABSTRACT

The disclosure provides at compounds of Formula I, compositions comprising the same, and methods of using the same, including use in treating diseases, disorders of conditions mediated by the signaling of formyl peptide receptor 1 (FPR1).

I

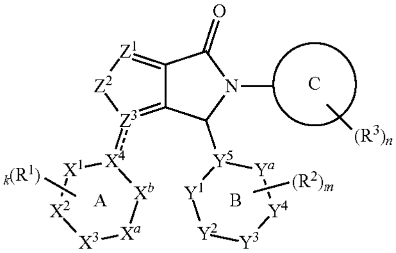

35 Claims, 1 Drawing Sheet

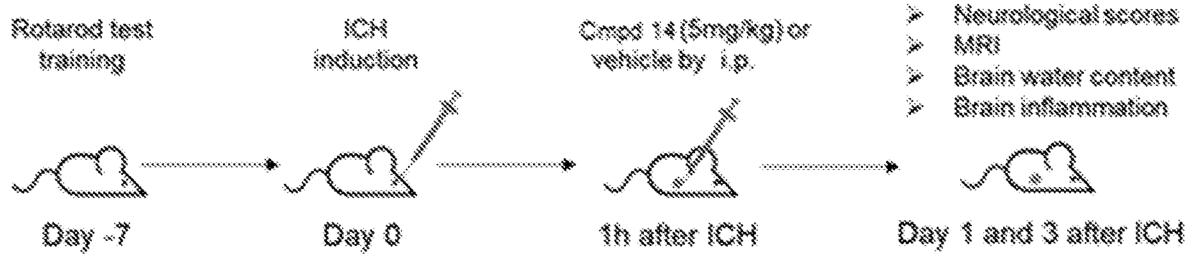
Rotarod test training
ICH induction
Cmpd 14 (5mg/kg) or vehicle by i.p.
Neurological scores
MRI
Brain water content
Brain inflammation
Day -7
Day 0
1h after ICH
Day 1 and 3 after ICH

MODULATORS OF FPR1 AND METHODS OF USING THE SAME

CROSS-REFERENCE TO RELATED APPLICATION

This is a national stage application of International Application No. PCT/CN2021/073155, filed Jan. 21, 2021, the content of which is incorporated herein by reference.

FIELD OF THE INVENTION

This disclosure relates to compounds that are useful for the treatment of diseases. More specifically, this disclosure relates to compounds that bind to formyl peptide receptors (FPR), such as FPR1, to modulate their activities in order to reduce or eliminate disproportionate FPR-mediated signaling, which is the underlying pathogenesis for an array of diseases, including, for example, diseases or disorders of the central nervous system (CNS) such as stroke, traumatic brain injury (TBI), glioblastomas and malignant gliomas.

BACKGROUND OF THE INVENTION

The restoration of body homeostasis after injuries or pathogen infections is critical to ensure the survival of an organism. The physiological wound healing and innate immune responses are initiated by the release of soluble mediators from the invading pathogen or injured lesions. The temperally regulated interactive repairing processes involve, for example, many chemokines, cytokines, acute phase proteins, infiltrating and residential cells, fibroblasts, nerve cells, and vasculature. If the injury persists or is of an extensive magnitude, the physiological wound repairing or anti-infection responses can become pathological, leading to excessive inflammation, edema, unwarranted fibrogenic repair, organ dysfunction, acute respiratory distress syndrome (ARDS), sepsis, ultimately organ failure and/or death. Therefore, effective regulations of the magnitude and the duration of the inflammation and resolution responses can be critical in the injury repair. After tissue injury or pathogen infection (by bacteria, virus, fungus, and/or microbes), a set of formyl-peptides, damage-associated molecular pattern molecules (DMAPs), inflammatory lipid mediators (such as leukotrienes and lipoxins), and acute phase proteins (such as annexins) are released from the invading pathogens, the injured cells, and the lesion tissues. Three formyl peptide receptors (FPR1, FPR2, and FPR3) serve as the key sensors for these chemotactic and activating molecules in humans. These FPR receptors are highly expressed on neutrophils, macrophages, T lymphocytes, dendritic cells, epithelial cells, fibroblasts, microglia, and astrocytes. The binding of these chemo-active molecules and acute proteins to the FPR receptors recruit leukocytes, stimulate superoxide and cytokine production, activate microglia, astrocytes, and other inflammatory and resolution responses for injury repair and host defense.

On the other hand, the pathological inflammatory responses from a disproportionate FPR receptor-mediated signaling are causal to multiple disease states after injury or infection, including, for example, the brain edema, function impairment, and organ failure after stroke or traumatic brain injury. In addition, the chronic activation of the FPR receptor-mediated signaling from invading pathogen, tissue stress, and tissue injury have been implicated to contribute to the pathogenesis of brain cancer, gastric cancer, and Parkinson syndrome.

Stroke is a leading cause of death globally with limited treatment options. The FPR receptors are highly expressed in microglia, astrocytes, and brain vasculature. After the onset of the induced intracerebral hemorrhage (ICH), the infiltrating leukocytes, activated platelet, microglia, and astrocytes release a spectrum of pro-inflammatory mediators, acute phase proteins, and DMAPs from the dying cells. The FPR1-activation induced leukocytes infiltration, reactive oxygen species (ROS) production, and cytokine releases can be the initial wave of inflammatory responses following the injury, contributing to the development of perihematomal edema and the aggravated mass effect in stroke.

Traumatic brain injury (TBI) is a leading cause of disability worldwide. The global incidence rate of TBI is estimated at 200 per 100 000 people per year. Severe injuries frequently lead to behavior disabilities, cerebral atrophy, dementia, permanent damage, and ultimately death. TBI has limited treatment option and FPR1 activation is involved in mediating the initial inflammatory processes of TBI.

Glioblastomas and malignant gliomas are the most common primary brain tumors. With an annual incidence of about 6 per 100,000 population, malignant glioma has no effective treatment at present. FPR1 receptor is highly expressed in glial cells, astrocytes, and brain vasculature. The FPR receptor interactions with the chemotactic ligands from injury, stress, and pathogens are implicated in the pathophysiology of the brain cancers.

In view of the foregoing, there remains a need for new therapeutic agents and alternative mechanisms that can effectively address the limited effective treatment options currently available for at least stroke, TBI, glioblastomas, and gliomas.

SUMMARY OF THE INVENTION

One aspect of this disclosure provides a compound selected from compounds of Formulae I, IIa, IIb, III, IV, V, VI, and VII, a tautomer thereof, a deuterated derivative of the compound or the tautomer, or a pharmaceutically acceptable salt of the foregoing, which can be employed in the treatment of diseases mediated by the signaling of formyl peptide receptor 1 (FPR1). For example, disclosed herein is a compound of the following structural Formula I:

Formula I

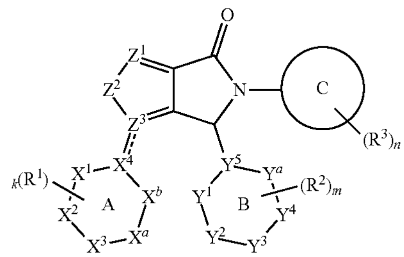

a tautomer thereof, a deuterated derivative of the compound or the tautomer, or a pharmaceutically acceptable salt of the foregoing, wherein:

$Z^1$ and $Z^2$ are both each O or N and $Z^3$ is C or N; wherein:

when $Z^3$ is C, then either $Z^1$ is O and $Z^2$ is N or $Z^1$ is N and $Z^2$ is O;

when $Z^3$ is N, then $Z^1$ and $Z^2$ are both N;

------ connecting Ring A to the rest of formula I is either absent such that Formula I comprises a spirocyclic ring system or ------ is a single bond;

Ring A is an aromatic or non-aromatic ring, wherein:

$X^a$ and $X^b$ are each independently C, N, or a bond; and $X^1$, $X^2$, $X^3$, and $X^4$ are each independently C or N;

Ring B is an aromatic or non-aromatic ring, wherein:

$Y^a$ is C, N, absent or a bond; and $Y^1$, $Y^2$, $Y^3$, $Y^4$, and $Y^5$ are each independently C or N;

Ring C is selected from $C_3$-$C_{12}$ carbocyclyl, 3 to 12-membered heterocyclyl, phenyl, and 5 to 10-membered heteroaryl;

$R^1$, $R^2$, and $R^3$, for each occurrence, is independently selected from halogen, cyano, $C_1$-$C_6$ alkyl, $C_2$-$C_6$ alkenyl, $C_1$-$C_6$ alkoxy, —C(═O)($C_1$-$C_6$ alkyl), (C(═O)$NR^hR^i$, —$NR^hR^i$, —$NR^h$C(═O)$R^k$, —$NR^h$C(═O)$OR^k$, —$NR^h$C(═O)$NR^iR^j$, —$NR^h$S(═O)$_p$$R^k$, —$OR^k$, —OC(═O)$R^k$, —OC(═O)$OR^k$, —OC(═O)$NR^hR^i$, —S(═O)$_p$$R^k$, —S(═O)$_p$$NR^hR^i$, $C_3$-$C_{12}$ carbocyclyl, 3 to 12-membered heterocyclyl, phenyl, and 5 to 10-membered heteroaryl;

wherein:

the $C_1$-$C_6$ alkyl, the $C_2$-$C_6$ alkenyl, and the $C_1$-$C_6$ alkoxy of any one of $R^1$, $R^2$, and $R^3$ and the $C_1$-$C_6$ alkyl of —C(═O)($C_1$-$C_6$ alkyl) are each optionally substituted with 1 to 3 groups selected from halogen, cyano, —C(═O)$R^h$, —C(═O)$OR^h$, —C(═O)$NR^hR^i$, —$NR^hR^i$, —$NR^h$C(═O)$R^k$, —$NR^h$C(═O)$OR^k$, —$NR^h$C(═O)$NR^iR^j$, —$NR^h$S(═O)$_p$$R^k$, —$OR^k$, —OC(═O)$R^k$, —OC(═O)$OR^k$, —OC(═O)$NR^hR^i$, —S(═O)$_p$$R^k$, —S(═O)$_p$$NR^hR^i$, and $C_3$-$C_6$ cycloalkyl;

the $C_3$-$C_{12}$ carbocyclyl, the 3 to 12-membered heterocyclyl, the phenyl, the 5 to 10-membered heteroaryl of any one of $R^1$, $R^2$, and $R^3$ are each optionally substituted with 1 to 3 groups selected from halogen, cyano, $C_1$-$C_4$ alkyl, —$NR^hR^i$, and —$OR^k$;

$R^h$, $R^i$, and $R^j$, for each occurrence, are each independently selected from hydrogen, $C_1$-$C_4$ alkyl, and $C_3$-$C_6$ cycloalkyl; wherein:

the $C_1$-$C_4$ alkyl of any one of $R^h$, $R^i$, and $R^j$ is optionally substituted with 1 to 3 groups selected from halogen, cyano, and —OH;

$R^k$, for each occurrence, are each independently selected from hydrogen, $C_1$-$C_4$ alkyl, and $C_3$-$C_6$ cycloalkyl; wherein: the $C_1$-$C_4$ alkyl of any one of $R^h$, $R^i$, and $R^j$ is optionally substituted with 1 to 3 groups selected from halogen, cyano, and —OH;

k and m are each independently an integer selected from 0, 1, 2, 3, 4, 5, and 6;

n is an integer selected from 0, 1, 2, 3, 4, and 5; and p is an integer selected from 1 and 2.

In one aspect of the disclosure, the compounds of Formula I are selected from Compounds 1 to 4 shown below, a tautomer thereof, a deuterated derivative of the compound or the tautomer, or a pharmaceutically acceptable salt of the foregoing.

In some embodiments, the disclosure provides pharmaceutical compositions comprising a compound of Formulae I, IIa, IIb, III, IV, V, VI, and VII, a tautomer thereof, a deuterated derivative of the compound or the tautomer, or a pharmaceutically acceptable salt of the foregoing, and a pharmaceutically acceptable carrier. In some embodiments, the pharmaceutical compositions may comprise a compound selected from Compounds 1 to 4 shown below, a tautomer thereof, a deuterated derivative of the compound or the tautomer, or a pharmaceutically acceptable salt of the foregoing. These compositions may further comprise an additional active pharmaceutical agent.

Another aspect of the disclosure provides methods of treating a disease, a disorder, or a condition mediated by the signaling of formyl peptide receptor 1 (FPR1) in a subject, comprising administering a therapeutically effective amount of a compound of Formulae I, IIa, IIb, III, IV, V, VI, and VII, a tautomer thereof, a deuterated derivative of the compound or the tautomer, or a pharmaceutically acceptable salt of the foregoing, or a pharmaceutical composition comprising any of the foregoing. In some embodiments, the methods of treatment comprise administering to a subject, a compound selected from Compounds 1 to 4 shown below, a tautomer thereof, a deuterated derivative of the compound or the tautomer, or a pharmaceutically acceptable salt of the foregoing, or a pharmaceutical composition comprising any of the foregoing.

In some embodiments, the methods of treatment comprise administration of an additional active pharmaceutical agent to the subject in need thereof, either in the same pharmaceutical composition as a compound of Formulae I, IIa, IIb, III, IV, V, VI, and VII, a tautomer thereof, a deuterated derivative of the compound or the tautomer, or a pharmaceutically acceptable salt of the foregoing, or in a separate composition. In some embodiments, the methods of treatment comprise administering a compound selected from Compounds 1 to 4 shown below, a tautomer thereof, a deuterated derivative of the compound or the tautomer, or a pharmaceutically acceptable salt of the foregoing with at least one additional active pharmaceutical agent either in the same composition or in a separate composition.

Also disclosed herein are methods of modulating FPR1 activities, comprising administering to a subject a therapeutically effective amount of a compound of Formulae I, IIa, IIb, III, IV, V, VI, and VII, a tautomer thereof, a deuterated derivative of the compound or the tautomer, or a pharmaceutically acceptable salt of the foregoing, or a pharmaceutical composition comprising any of the foregoing. In some embodiments, the methods of modulating FPR1 comprise administering to a subject, a compound selected from Compounds 1 to 4 shown below, a tautomer thereof, a deuterated derivative of the compound or the tautomer, or a pharmaceutically acceptable salt of the foregoing, or a pharmaceutical composition comprising any of the foregoing. In some embodiments, the methods of modulating FPR1 activity comprise contacting said FPR1 with a compound of Formulae I, IIa, IIb, III, IV, V, VI, and VII, a tautomer thereof, a deuterated derivative of the compound or the tautomer, or a pharmaceutically acceptable salt of the foregoing, or a pharmaceutical composition comprising any of the foregoing. In some embodiments, the methods of modulating FPR1 comprise contacting said FPR1 with a compound selected from Compounds 1 to 4 shown below, a tautomer thereof, a deuterated derivative of the compound or the tautomer, or a pharmaceutically acceptable salt of the foregoing, or a pharmaceutical composition comprising any of the foregoing.

BRIEF DESCRIPTION OF THE DRAWINGS

FIG. 1 is a schematic diagram depicting the procedures for evaluating the efficacy of the compounds disclosed herein in the induced intracerebral hemorrhage (ICH) mouse model.

DETAILED DESCRIPTION

I. Definitions

The term "a" or "an" when referring to a noun as used herein encompasses the expression "at least one" and therefore encompasses both singular and plural units of the noun. For example, "an additional pharmaceutical agent" means a single or two or more additional pharmaceutical agents.

The term "FPR1" or "formyl peptide receptor 1" as used herein means the cell surface receptor protein that is encoded by the FPR1 gene in humans. FPR1 regulates a wide variety of neutrophil functional responses and plays an important role in the pathogenesis of various diseases, including, for example, the diseases set forth above.

The term "FPR1 modulator" as used herein refers to an organic chemistry small molecule compound (≤10 kDa) that has the ability to alter any one or more immune responses or signalings mediated by FPR1 from their native state, and can be either an FPR1 agonist or an FPR1 antagonist. If an FPR1 modulator is an agonist, the compound has the ability to increase any one or more immune responses or signalings mediated by FPR1 from their native state, for example, by binding to the receptor to activate the receptor. If an FPR1 modulator is an antagonist, the compound has the ability to reduce or inhibit any one or more immune responses or signalings mediated by FPR1 from their native state, for example, by blocking the agonist binding site on the receptor in order to achieve the reduced or inhibited effects.

The term "compound," when referring to a compound of this disclosure, refers to a collection of molecules having an identical chemical structure unless otherwise indicated as a collection of stereoisomers (for example, a collection of racemates, a collection of cis/trans stereoisomers, or a collection of (E) and (Z) stereoisomers), except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this disclosure will depend upon a number of factors, including, for example, the isotopic purity of reagents used to make the compound and the efficiency of incorporation of isotopes in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

As used herein, "optionally substituted" is interchangeable with the phrase "substituted or unsubstituted." In general, the term "substituted," refers to the replacement of hydrogen radicals in a given structure with the radical of a specified substituent. Unless otherwise indicated, an "optionally substituted" group may have a substituent at each substitutable position of the group, and when more than one position in any given structure may be substituted with more than one substituent chosen from a specified group, the substituent may be either the same or different at every position. Combinations of substituents envisioned by this disclosure are those that result in the formation of stable or chemically feasible compounds.

The term "isotopologue" refers to a species in which the chemical structure differs from only in the isotopic composition thereof. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$ or $^{14}C$ are within the scope of this disclosure.

Unless otherwise indicated, structures depicted herein are also meant to include all isomeric forms of the structure, e.g., racemic mixtures, cis/trans isomers, geometric (or conformational) isomers, such as (Z) and (E) double bond isomers, and (Z) and (E) conformational isomers. Therefore, geometric and conformational mixtures of the present compounds are within the scope of the disclosure. Unless otherwise stated, all tautomeric forms of the compounds of the disclosure are within the scope of the disclosure.

The term "tautomer," as used herein, refers to one of two or more isomers of compound that exist together in equilibrium, and are readily interchanged by migration of an atom, e.g., a hydrogen atom, or group within the molecule.

"Stereoisomer" as used herein refers to enantiomers and diastereomers.

As used herein, "deuterated derivative" refers to a compound having the same chemical structure as a reference compound, but with one or more hydrogen atoms replaced by a deuterium atom ("D" or "$^2H$"). It will be recognized that some variation of natural isotopic abundance occurs in a synthesized compound depending on the origin of chemical materials used in the synthesis. The concentration of naturally abundant stable hydrogen isotopes, notwithstanding this variation is small and immaterial as compared to the degree of stable isotopic substitution of deuterated derivatives described herein. Thus, unless otherwise stated, when a reference is made to a "deuterated derivative" of a compound of the disclosure, at least one hydrogen is replaced with deuterium at a level that is well above its natural isotopic abundance, which is typically about 0.015%. In some embodiments, the deuterated derivatives disclosed herein have an isotopic enrichment factor for each deuterium atom, of at least 3500 (52.5% deuterium incorporation at each designated deuterium), at least 4500 (67.5% deuterium incorporation at each designated deuterium), at least 5000 (75% deuterium incorporation at each designated deuterium), at least 5500 (82.5% deuterium incorporation at each designated deuterium), at least 6000 (90% deuterium incorporation at each designated deuterium), at least 6333.3 (95% deuterium incorporation at each designated deuterium), at least 6466.7 (97% deuterium incorporation at each designated deuterium), or at least 6600 (99% deuterium incorporation at each designated deuterium).

The term "isotopic enrichment factor" as used herein means the ratio between the isotopic abundance and the natural abundance of a specified isotope.

The term "alkyl" as used herein, means a linear or branched, substituted or unsubstituted hydrocarbon chain that is completely saturated. Unless otherwise specified, an alkyl group contains 1 to 30 alkyl carbon atoms. In some embodiments, an alkyl group contains 1 to 20 alkyl carbon atoms. In some embodiments, an alkyl group contains 1 to 10 aliphatic carbon atoms. In some embodiments, an alkyl group contains 1 to 8 aliphatic carbon atoms. In some embodiments, an alkyl group contains 1 to 6 alkyl carbon atoms. In some embodiments, an alkyl group contains 1 to 4 alkyl carbon atoms. In other embodiments, an alkyl group contains 1 to 3 alkyl carbon atoms. And in yet other embodiments, an alkyl group contains 1 to 2 alkyl carbon atoms. In some embodiments, alkyl groups are substituted. In some embodiments, alkyl groups are unsubstituted. In some embodiments, alkyl groups are linear or straight-chain or unbranched. In some embodiments, alkyl groups are branched.

The term "cycloalkyl" refers to a monocyclic $C_{3-8}$ hydrocarbon or a spirocyclic, fused, or bridged bicyclic or tricyclic $C_{8-14}$ hydrocarbon that is completely saturated, wherein any individual ring in said bicyclic ring system has 3 to 7 members. In some embodiments, cycloalkyl groups are substituted. In some embodiments, cycloalkyl groups are unsubstituted. In some embodiments, the cycloalkyl is a $C_3$ to $C_{12}$ cycloalkyl. In some embodiments, the cycloalkyl is a $C_3$ to $C_8$ cycloalkyl. In some embodiments, the cycloalkyl is a $C_3$ to $C_6$ cycloalkyl. Non-limiting examples of monocyclic cycloalkyls include cyclopropyl, cyclobutyl, cyclopentanyl, and cyclohexyl.

The term "carbocyclyl" encompasses the term "cycloalkyl" and refers to a monocyclic $C_{3-8}$ hydrocarbon or a spirocyclic, fused, or bridged bicyclic or tricyclic $C_{8-14}$ hydrocarbon that is completely saturated, or is partially saturated as it contains one or more units of unsaturation but is not aromatic, wherein any individual ring in said bicyclic ring system has 3 to 7 members. Bicyclic carbocyclyls include combinations of a monocyclic carbocyclic ring fused to, for example, a phenyl. In some embodiments, carbocyclyl groups are substituted. In some embodiments, carbocyclyl groups are unsubstituted. In some embodiments, the carbocyclyl is a $C_3$ to $C_{12}$ carbocyclyl. In some embodiments, the carbocyclyl is a $C_3$ to $C_{10}$ carbocyclyl. In some embodiments, the carbocyclyl is a $C_3$ to $C_8$ carbocyclyl.

The term "alkenyl" as used herein, means a linear or branched, substituted or unsubstituted hydrocarbon chain that contains one or more double bonds. In some embodiments, alkenyl groups are substituted. In some embodiments, alkenyl groups are unsubstituted. In some embodiments, alkenyl groups are linear, straight-chain, or unbranched. In some embodiments, alkenyl groups are branched.

The term "heterocyclyl" as used herein means non-aromatic (i.e., completely saturated or partially saturated as in it contains one or more units of unsaturation but is not aromatic), monocyclic, or spirocyclic, fused, or bridged bicyclic or tricyclic ring systems in which one or more ring members is an independently chosen heteroatom. Bicyclic heterocyclyls include, for example, the following combinations of monocyclic rings: a monocyclic heteroaryl fused to a monocyclic heterocyclyl; a monocyclic heterocyclyl fused to another monocyclic heterocyclyl; a monocyclic heterocyclyl fused to phenyl; a monocyclic heterocyclyl fused to a monocyclic carbocyclyl/cycloalkyl; and a monocyclic heteroaryl fused to a monocyclic carbocyclyl/cycloalkyl. In some embodiments, the "heterocyclyl" group contains 3 to 14 ring members in which one or more ring members is a heteroatom independently chosen, for example, from oxygen, sulfur, nitrogen, and phosphorus. In some embodiments, each ring in a bicyclic or tricyclic ring system contains 3 to 7 ring members. In some embodiments, the heterocycle has at least one unsaturated carbon-carbon bond. In some embodiments, the heterocycle has at least one unsaturated carbon-nitrogen bond. In some embodiments, the heterocycle has one heteroatom independently chosen from oxygen, sulfur, nitrogen, and phosphorus. In some embodiments, the heterocycle has one heteroatom that is a nitrogen atom. In some embodiments, the heterocycle has one heteroatom that is an oxygen atom. In some embodiments, the heterocycle has two heteroatoms that are each independently selected from nitrogen and oxygen. In some embodiments, the heterocycle has three heteroatoms that are each independently selected from nitrogen and oxygen. In some embodiments, heterocycles are substituted. In some embodiments, heterocycles are unsubstituted. In some embodiments, the heterocyclyl is a 3- to 12-membered heterocyclyl. In some embodiments, the heterocyclyl is a 4- to 10-membered heterocyclyl. In some embodiments, the heterocyclyl is a 3- to 8-membered heterocyclyl. In some embodiments, the heterocyclyl is a 5- to 10-membered heterocyclyl. In some embodiments, the heterocyclyl is a 5- to 8-membered heterocyclyl. In some embodiments, the heterocyclyl is a 5- or 6-membered heterocyclyl. In some embodiments, the heterocyclyl is a 6-membered heterocyclyl. Non-limiting examples of monocyclic heterocyclyls include piperidinyl, piperazinyl, tetrahydropyranyl, azetidinyl, tetrahydrothiophenyl 1,1-dioxide, etc.

The term "heteroatom" means one or more of oxygen, sulfur, and nitrogen, including, any oxidized form of nitrogen or sulfur, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "unsaturated", as used herein, means that a moiety has one or more units or degrees of unsaturation. Unsaturation is the state in which not all of the available valence bonds in a compound are satisfied by substituents and thus the compound contains double or triple bonds.

The term "alkoxy" as used herein, refers to an alkyl group, as defined above, wherein one carbon of the alkyl group is replaced by an oxygen ("alkoxy") atom, provided that the oxygen atom is linked between two carbon atoms.

The term "halogen" includes F, Cl, Br, and I, i.e., fluoro, chloro, bromo, and iodo, respectively.

As used herein, a "cyano" or "nitrile" group refer to —C≡N.

As used herein, an "aromatic ring" refers to a carbocyclic or heterocyclic ring that contains conjugated, planar ring systems with delocalized pi electron orbitals comprised of [4n+2] p orbital electrons, wherein n is an integer of 0 to 6. A "non-aromatic" ring refers to a carbocyclic or heterocyclic that does not meet the requirements set forth above for an aromatic ring, and can be either completely or partially saturated. Nonlimiting examples of aromatic rings include aryl and heteroaryl rings that are further defined as follows.

The term "aryl" used alone or as part of a larger moiety as in "arylalkyl," "arylalkoxy," or "aryloxyalkyl," refers to monocyclic or spirocyclic, fused, or bridged bicyclic or tricyclic ring systems having a total of five to fourteen ring members, wherein every ring in the system is an aromatic ring containing only carbon atoms and wherein each ring in a bicyclic or tricyclic ring system contains 3 to 7 ring members. Nonlimiting examples of aryl groups include phenyl ($C_6$) and naphthyl ($C_{10}$) rings. In some embodiments, aryl groups are substituted. In some embodiments, aryl groups are unsubstituted.

The term "heteroaryl" refers to monocyclic or spirocyclic, fused, or bridged bicyclic or tricyclic ring systems having a total of five to fourteen ring members, wherein at least one ring in the system is aromatic, at least one ring in the system contains one or more heteroatoms, and wherein each ring in a bicyclic or tricyclic ring system contains 3 to 7 ring members. Bicyclic heteroaryls include, for example, the following combinations of monocyclic rings: a monocyclic heteroaryl fused to another monocyclic heteroaryl; and a monocyclic heteroaryl fused to a phenyl. In some embodiments, heteroaryl groups are substituted. In some embodiments, heteroaryl groups have one or more heteroatoms chosen, for example, from nitrogen, oxygen, and sulfur. In some embodiments, heteroaryl groups have one heteroatom. In some embodiments, heteroaryl groups have two heteroatoms. In some embodiments, heteroaryl groups are monocyclic ring systems having five ring members. In some embodiments, heteroaryl groups are monocyclic ring systems having six ring members. In some embodiments, heteroaryl groups are unsubstituted. In some embodiments, the heteroaryl is a 3- to 12-membered heteroaryl. In some embodiments, the heteroaryl is a 3- to 10-membered heteroaryl. In some embodiments, the heteroaryl is a 3- to 8-membered heteroaryl. In some embodiments, the heteroaryl is a 5- to 10-membered heteroaryl. In some embodiments, the heteroaryl is a 5- to 8-membered heteroaryl. In some embodiments, the heteroaryl is a 5- or 6-membered heteroaryl. Non-limiting examples of monocyclic heteroaryls are pyridinyl, pyrimidinyl, thiophenyl, thiazolyl, isoxazolyl, etc.

A "spirocyclic ring system" refers to a ring system having two or more cyclic rings, where every two rings share only one common atom.

Non-limiting examples of suitable solvents that may be used in this disclosure include water, methanol (MeOH), ethanol (EtOH), dichloromethane or "methylene chloride" ($CH_2Cl_2$), toluene, acetonitrile (MeCN), dimethylformamide (DMF), dimethyl sulfoxide (DMSO), methyl acetate (MeOAc), ethyl acetate (EtOAc), heptanes, isopropyl acetate (IPAc), tert-butyl acetate (t-BuOAc), isopropyl alcohol (IPA), tetrahydrofuran (THF), 2-methyl tetrahydrofuran (2-Me THF), methyl ethyl ketone (MEK), tert-butanol, diethyl ether ($Et_2O$), methyl-tert-butyl ether (MTBE), 1,4-dioxane, and N-methyl pyrrolidone (NMP).

Non-limiting examples of suitable bases that may be used in this disclosure include 1,8-diazabicyclo[5.4.0]undec-7-ene (DBU), potassium tert-butoxide (KOtBu), potassium carbonate ($K_2CO_3$), N-methylmorpholine (NMM), triethylamine ($Et_3N$; TEA), diisopropyl-ethyl amine (i-$Pr_2EtN$; DIPEA), pyridine, potassium hydroxide (KOH), sodium hydroxide (NaOH), lithium hydroxide (LiOH) and sodium methoxide (NaOMe; $NaOCH_3$).

Disclosed herein are pharmaceutically acceptable salts of the disclosed compounds. A salt of a compound is formed between an acid and a basic group of the compound, such as an amino functional group, or a base and an acidic group of the compound, such as a carboxyl functional group.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this disclosure. Suitable pharmaceutically acceptable salts are, for example, those disclosed in S. M. Berge, et al. *J. Pharmaceutical Sciences,* 1977, 66, pp. 1 to 19.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In some embodiments, pharmaceutically acceptable acid addition salts include those formed with mineral acids such as hydrochloric acid and hydrobromic acid, and those formed with organic acids such as maleic acid.

Pharmaceutically acceptable salts derived from appropriate bases include alkali metal, alkaline earth metal, ammonium, and $N^+(C_{1-4}alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

The term "subject" refers to an animal, including but not limited to, a human.

The term "therapeutically effective amount" refers to that amount of a compound that produces the desired effect for which it is administered (e.g., improvement in symptoms of diseases, disorders, and conditions mediated by the signaling of FPR1, lessening the severity of diseases, disorders, and conditions mediated by the signaling of FPR1 or a symptom thereof, and/or reducing progression of diseases, disorders, and conditions mediated by the signaling of FPR1 or a symptom thereof). The exact amount of a therapeutically effective amount will depend on the purpose of the treatment and will be ascertainable by one skilled in the art using known techniques (see, e.g., Lloyd (1999), The Art, Science and Technology of Pharmaceutical Compounding).

As used herein, the term "treatment" and its cognates refer to slowing or stopping disease progression. "Treatment" and its cognates as used herein include, but are not limited to the following: complete or partial remission, lower risk of diseases, disorders, and conditions mediated by FPR1 signaling, and disease-related complications. Improvements in or lessening the severity of any of these symptoms can be readily assessed according to methods and techniques known in the art or subsequently developed.

The terms "about" and "approximately," when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent.

II. Compounds and Compositions

In a first embodiment, a compound of this disclosure is a compound of the following structural formula I:

Formula I

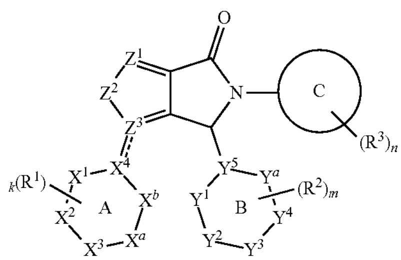

a tautomer thereof, a deuterated derivative of the compound or the tautomer, or a pharmaceutically acceptable salt of the foregoing, wherein:

- $Z^1$ and $Z^2$ are both each O or N and $Z^3$ is C or N; wherein:
  - when $Z^3$ is C, then either $Z^1$ is O and $Z^2$ is N or $Z^1$ is N and $Z^2$ is O;
  - when $Z^3$ is N, then $Z^1$ and $Z^2$ are both N;
- ------ connecting Ring A to the rest of formula I is either absent such that Formula I comprises a spirocyclic ring system or ------ is a single bond;
- Ring A is an aromatic or non-aromatic ring, wherein:
  - $X^a$ and $X^b$ are each independently C, N, or a bond; and $X^1$, $X^2$, $X^3$, and $X^4$ are each independently C or N;
- Ring B is an aromatic or non-aromatic ring, wherein:
  - $Y^a$ is C, N, absent or a bond; and
  - $Y^1$, $Y^2$, $Y^3$, $Y^4$, and $Y^5$ are each independently C or N;
- Ring C is selected from $C_3$-$C_{12}$ carbocyclyl, 3 to 12-membered heterocyclyl, phenyl, and 5 to 10-membered heteroaryl;
- $R^1$, $R^2$, and $R^3$, for each occurrence, is independently selected from halogen, cyano, $C_1$-$C_6$ alkyl, $C_2$-$C_6$ alkenyl, $C_1$-$C_6$ alkoxy, —C(═O)($C_1$-$C_6$ alkyl), (C(═O)$NR^hR^i$, —$NR^hR^i$, —$NR^hC$(═O)$R^k$, —$NR^hC$(═O)OR, —$NR^hC$(═O)$NR^iR^j$, —$NR^hS$(═O)$_pR^k$, —$OR^k$, —OC(═O)$R^k$, —OC(═O)$OR^k$, —OC(═O)$NR^hR^i$, —S(═O)$_pR^k$, —S(═O)$_pNR^hR^i$, $C_3$-$C_{12}$ carbocyclyl, 3 to 12-membered heterocyclyl, phenyl, and 5 to 10-membered heteroaryl;

wherein:

the $C_1$-$C_6$ alkyl, the $C_2$-$C_6$ alkenyl, and the $C_1$-$C_6$ alkoxy of any one of $R^1$, $R^2$, and $R^3$ and the $C_1$-$C_6$ alkyl of —C(═O)($C_1$-$C_6$ alkyl) are each optionally substituted with 1 to 3 groups selected from halogen, cyano, —C(═O)$R^h$, —C(═O)$OR^h$, —C(═O)$NR^hR^i$, —$NR^hR^i$, —$NR^hC$(═O)$R^k$, —$NR^hC$(═O)$OR^k$, —$NR^hC$(═O)$NR^iR^j$, —$NR^hS$(═O)$_pR^k$, —$OR^k$, —OC(═O)$R^h$, —OC(═O)$OR^h$, —OC(═O)$NR^hR^i$, —S(═O)$_pR^k$, —S(═O)$_pNR^hR^i$, and $C_3$-$C_6$ cycloalkyl;

the $C_3$-$C_{12}$ carbocyclyl, the 3 to 12-membered heterocyclyl, the phenyl, the 5 to 10-membered heteroaryl of any one of $R^1$, $R^2$, and $R^3$ are each optionally substituted with 1 to 3 groups selected from halogen, cyano, $C_1$-$C_4$ alkyl, —$NR^hR^i$, and —$OR^k$;

$R^h$, $R^i$, and $R^j$, for each occurrence, are each independently selected from hydrogen, $C_1$-$C_4$ alkyl, and $C_3$-$C_6$ cycloalkyl; wherein:

the $C_1$-$C_4$ alkyl of any one of $R^h$, $R^i$, and $R^j$ is optionally substituted with 1 to 3 groups selected from halogen, cyano, and —OH;

$R^k$, for each occurrence, are each independently selected from hydrogen, $C_1$-$C_4$ alkyl, and $C_3$-$C_6$ cycloalkyl; wherein: the $C_1$-$C_4$ alkyl of any one of $R^h$, $R^i$, and $R^j$ is optionally substituted with 1 to 3 groups selected from halogen, cyano, and —OH;

k and m are each independently an integer selected from 0, 1, 2, 3, 4, 5, and 6;

n is an integer selected from 0, 1, 2, 3, 4, and 5; and p is an integer selected from 1 and 2.

In a second embodiment, a compound of the disclosure is of one of the following structural formulae IIa or IIb:

Formumla IIa

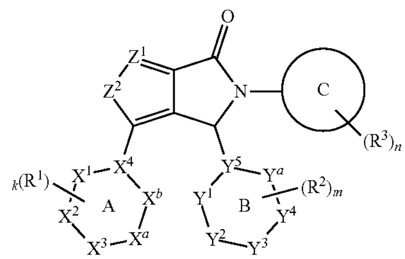

Formula IIb

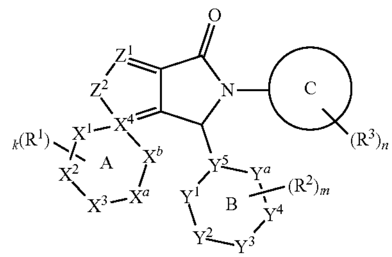

a tautomer thereof, a deuterated derivative of the compound or the tautomer, or a pharmaceutically acceptable salt of the foregoing; and all other variables not specifically defined herein are as defined in the first embodiment.

In a third embodiment, a compound of the disclosure is of the following structural formula III:

Formula III

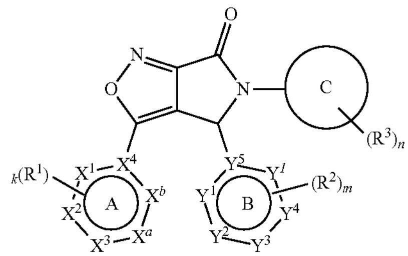

a tautomer thereof, a deuterated derivative of the compound or the tautomer, or a pharmaceutically acceptable salt of the foregoing; wherein Ring A and Ring B are each an aromatic ring; and all other variables not specifically defined herein are as defined in any one of the first and second embodiments.

In a fourth embodiment, a compound of the disclosure is of the following structural formula IV:

Formula IV

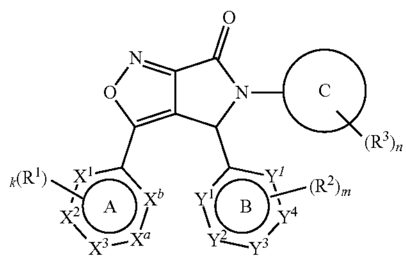

a tautomer thereof, a deuterated derivative of the compound or the tautomer, or a pharmaceutically acceptable salt of the foregoing; wherein:

no more than 3 of $X^a$, $X^b$, $X^1$, $X^2$, and $X^3$ are N; and no more than 3 of $Y^a$, $Y^1$, $Y^2$, $Y^3$, and $Y^4$ are N;

and all other variables not specifically defined herein are as defined in any one of the first, second, and third embodiments.

In a fifth embodiment, in a compound, tautomer, deuterated derivative, or pharmaceutically acceptable salt of this disclosure:

no more than 2 of $X^a$, $X^b$, $X^1$, $X^2$, and $X^3$ are N; and no more than 2 of $Y^a$, $Y^1$, $Y^2$, $Y^3$, and $Y^4$ are N;

and all other variables not specifically defined herein are as defined in any one of the first, second, third, and fourth embodiments.

In a sixth embodiment, in a compound, tautomer, deuterated derivative, or pharmaceutically acceptable salt of this disclosure:

$X^a$ and $X^b$ are each independently C or N; and $Y^a$ is C or N;

and all other variables not specifically defined herein are as defined in any one of the first, second, third, fourth, and fifth embodiments.

In a seventh embodiment, in a compound, tautomer, deuterated derivative, or pharmaceutically acceptable salt of this disclosure, Ring A is pyridinyl or pyrimidinyl substituted with k groups of $R^1$; and all other variables not specifically defined herein are as defined in any one of the first, second, third, fourth, fifth, and sixth embodiments.

In an eighth embodiment, a compound of the disclosure is of the following structural formula V:

Formula V

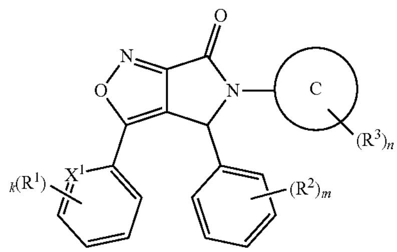

a tautomer thereof, a deuterated derivative of the compound or the tautomer, or a pharmaceutically acceptable salt of the foregoing; wherein $X^1$ is C or N; and all other variables not specifically defined herein are as defined in any one of the first, second, third, fourth, fifth, sixth, and seventh embodiments.

In a ninth embodiment, a compound of the disclosure is of the following structural formula VI:

Formula VI

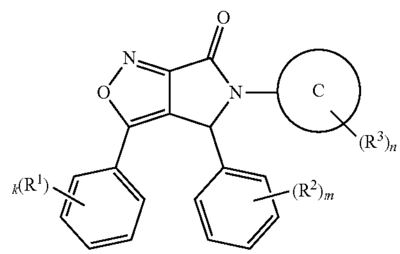

a tautomer thereof, a deuterated derivative of the compound or the tautomer, or a pharmaceutically acceptable salt of the foregoing; and all other variables not specifically defined herein are as defined in any one of the first, second, third, fourth, fifth, sixth, seventh, and eighth embodiments.

In a tenth embodiment, in a compound, tautomer, deuterated derivative, or pharmaceutically acceptable salt of this disclosure, Ring C is $C_5$-$C_6$ cycloalkyl or 5- to 6-membered heterocyclyl substituted with n groups of $R^3$; and all other variables not specifically defined herein are as defined in any one of the first, second, third, fourth, fifth, sixth, seventh, eighth, and ninth embodiments.

In an eleventh embodiment, in a compound, tautomer, deuterated derivative, or pharmaceutically acceptable salt of this disclosure, Ring C is $C_5$-$C_6$ cycloalkyl or 5- to 6-membered heterocyclyl substituted with n groups of $R^3$, wherein the 5- to 6-membered heterocyclyl contains 1 or 2 heteroatoms selected from O and N; and all other variables not specifically defined herein are as defined in any one of the first, second, third, fourth, fifth, sixth, seventh, eighth, ninth, and tenth embodiments.

In a twelfth embodiment, in a compound, tautomer, deuterated derivative, or pharmaceutically acceptable salt of this disclosure, Ring C is cyclohexyl or 6-membered heterocyclyl with n groups of $R^3$, wherein the 6-membered heterocyclyl contains 1 or 2 heteroatoms selected from O and N; and all other variables not specifically defined herein are as defined in any one of the first, second, third, fourth, fifth, sixth, seventh, eighth, ninth, tenth, and eleventh embodiments.

In a thirteenth embodiment, in a compound, tautomer, deuterated derivative, or pharmaceutically acceptable salt of this disclosure, Ring C is tetrahydro-2H-pyranyl substituted with n groups of $R^3$; and all other variables not specifically defined herein are as defined in any one of the first, second, third, fourth, fifth, sixth, seventh, eighth, ninth, tenth, eleventh, and twelfth embodiments.

In a fourteenth embodiment, a compound of the disclosure is of the following structural formula VII:

Formula VII

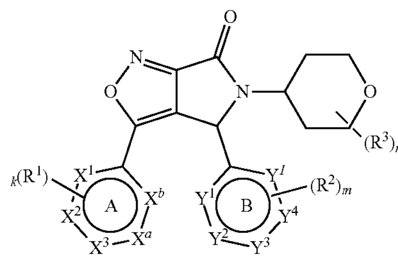

a tautomer thereof, a deuterated derivative of the compound or the tautomer, or a pharmaceutically acceptable salt of the foregoing; wherein:

Ring A and Ring B are each an aromatic ring;

no more than 3 of $X^a$, $X^b$, $X^1$, $X^2$, and $X^3$ are N; and no more than 3 of $Y^a$, $Y^1$, $Y^2$, $Y^3$, and $Y^4$ are N. and all other variables not specifically defined herein are as defined in any one of the first and second embodiments.

In a fifteenth embodiment, in a compound, tautomer, deuterated derivative, or pharmaceutically acceptable salt of this disclosure:

no more than 2 of $X^a$, $X^b$, $X^1$, $X^2$, and $X^3$ are N; and no more than 2 of $Y^a$, $Y^1$, $Y^2$, $Y^3$, and $Y^4$ are N;

and all other variables not specifically defined herein are as defined in the fourteenth embodiment.

In a sixteenth embodiment, in a compound, tautomer, deuterated derivative, or pharmaceutically acceptable salt of this disclosure:

$X^a$ and $X^b$ are each independently C or N; and $Y^a$ is C or N;

and all other variables not specifically defined herein are as defined in any one of the fourteenth and fifteenth embodiments.

In a seventeenth embodiment, in a compound, tautomer, deuterated derivative, or pharmaceutically acceptable salt of this disclosure, Ring A is pyridinyl or pyrimidinyl substituted with k groups of $R^i$; and all other variables not specifically defined herein are as defined in any one of the fourteenth, fifteenth, and sixteenth embodiments.

In an eighteenth embodiment, in a compound, tautomer, deuterated derivative, or pharmaceutically acceptable salt of this disclosure, Ring B is phenyl substituted with m groups of $R^2$; and all other variables not specifically defined herein are as defined in any one of the first, fourteenth, fifteenth, sixteenth, and seventeenth embodiments.

In a nineteenth embodiment, in a compound, tautomer, deuterated derivative, or pharmaceutically acceptable salt of this disclosure, $R^a$ is hydrogen or $C_1$-$C_2$ alkyl optionally substituted with 1 or 2 groups selected from halogen, —CN, and —OH; and all other variables not specifically defined herein are as defined in any one of the first, fourteenth, fifteenth, sixteenth, seventeenth, eighteenth, and nineteenth embodiments.

In a twentieth embodiment, in a compound, tautomer, deuterated derivative, or pharmaceutically acceptable salt of this disclosure, $R^a$ is hydrogen; and all other variables not specifically defined herein are as defined in any one of the first, fourteenth, fifteenth, sixteenth, seventeenth, eighteenth, and nineteenth embodiments.

In a twenty-first embodiment, in a compound, tautomer, deuterated derivative, or pharmaceutically acceptable salt of this disclosure, $R^1$, $R^2$, and $R^3$, for each occurrence, is independently selected from halogen, cyano, $C_1$-$C_6$ alkyl, $C_1$-$C_6$ alkoxy, —C(═O)($C_1$-$C_6$ alkyl), —C(═O)$NR^hR^i$, —$NR^hR^i$, —$OR^k$, —S(═O)$_2R^h$, —S(═O)$_2NR^hR^i$, $C_3$-$C_6$ cycloalkyl, 5 to 6-membered heterocyclyl, phenyl, and 5 to 6-membered heteroaryl;

wherein:

the $C_1$-$C_6$ alkyl and the $C_1$-$C_6$ alkoxy of any one of $R^1$, $R^2$, and $R^3$ and the $C_1$-$C_6$ alkyl of —C(═O)($C_1$-$C_6$ alkyl) are each optionally substituted with 1 to 3 groups selected from halogen, cyano, C(═O)$OR^k$, and —$OR^k$;

the $C_3$-$C_6$ cycloalkyl, the 5 to 6-membered heterocyclyl, the phenyl, and the 5 to 6-membered heteroaryl of any one of $R^1$, $R^2$, and $R^3$ are each optionally substituted with 1 to 3 groups selected from halogen, cyano, $C_1$-$C_4$ alkyl, and —$OR^k$;

$R^h$ and $R^i$ for each occurrence, are each independently selected from hydrogen and $C_1$-$C_4$ alkyl; wherein:

the $C_1$-$C_4$ alkyl of any one of $R^h$ and $R^i$ is optionally substituted with 1 to 3 groups selected from halogen, cyano, and —OH; and $R^k$, for each occurrence, are each independently selected from hydrogen and $C_1$-$C_4$ alkyl; wherein:

the $C_1$-$C_4$ alkyl of any one of $R^h$ and $R^i$ is optionally substituted with 1 to 3 groups selected from halogen, cyano, and —OH;

and all other variables not specifically defined herein are as defined in any one of the first, second, third, fourth, fifth, sixth, seventh, eighth, ninth, tenth, eleventh, twelfth, thirteenth, fourteenth, fifteenth, sixteenth, seventeenth, eighteenth, nineteenth, and twentieth embodiments.

In a twenty-second embodiment, in a compound, tautomer, deuterated derivative, or pharmaceutically acceptable salt of this disclosure, $R^1$, $R^2$, and $R^3$, for each occurrence, is independently selected from halogen, cyano, $C_1$-$C_4$ alkyl, $C_1$-$C_4$ alkoxy, —C(═O)($C_1$-$C_4$ alkyl), —C(═O)$NR^hR^i$, —$NR^hR^i$, and —$OR^k$; wherein:

the $C_1$-$C_4$ alkyl and the $C_1$-$C_4$ alkoxy of any one of $R^1$, $R^2$, and $R^3$ and the $C_1$-$C_4$ alkyl of —C(═O)($C_1$-$C_4$ alkyl) are each optionally substituted is optionally substituted with 1 to 3 groups selected from halogen, cyano, and —$OR^k$;

$R^h$ and $R^i$, for each occurrence, are each independently selected from hydrogen and $C_1$-$C_2$ alkyl; and $R^k$, for each occurrence, are each independently selected from hydrogen and $C_1$-$C_2$ alkyl;

and all other variables not specifically defined herein are as defined in any one of the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, and twenty-first embodiments.

In a twenty-third embodiment, in a compound, tautomer, deuterated derivative, or pharmaceutically acceptable salt of this disclosure, $R^1$, $R^2$, and $R^3$, for each occurrence, is independently selected from halogen, $C_1$-$C_4$ alkyl, $C_1$-$C_4$ alkoxy, —C(═O)($C_1$-$C_4$ alkyl), and —$OR^k$; wherein:

the $C_1$-$C_4$ alkyl of any one of $R^1$, $R^2$, and $R^3$ is optionally substituted is optionally substituted with 1 to 3 groups of halogen; and $R^k$, for each occurrence, are each independently selected from hydrogen and $C_1$-$C_2$ alkyl;

and all other variables not specifically defined herein are as defined in any one of the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, and twenty-second embodiments.

In a twenty-fourth embodiment, in a compound, tautomer, deuterated derivative, or pharmaceutically acceptable salt of this disclosure, $R^1$, for each occurrence, is independently selected from F, Cl, Br, $C_1$-$C_2$ alkyl, and —$OR^k$; wherein:

the $C_1$-$C_2$ alkyl of $R^1$ is optionally substituted is optionally substituted with 1 to 3 groups of halogen; and $R^k$, for each occurrence, are each independently selected from hydrogen and $C_1$-$C_2$ alkyl;

and all other variables not specifically defined herein are as defined in any one of the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, and twenty-third embodiments.

In a twenty-fifth embodiment, in a compound, tautomer, deuterated derivative, or pharmaceutically acceptable salt of this disclosure, $R^1$, for each occurrence, is independently selected from F, —$CH_3$, and —OH; and all other variables not specifically defined herein are as defined in any one of the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, and twenty-fourth embodiments.

In a twenty-sixth embodiment, in a compound, tautomer, deuterated derivative, or pharmaceutically acceptable salt of this disclosure, $R^2$, for each occurrence, is independently selected from F, Cl, Br, and $C_1$-$C_2$ alkyl; wherein:

the $C_1$-$C_2$ alkyl of $R^1$ is optionally substituted with 1 to 3 halogen; and all other variables not specifically defined herein are as defined in any one of the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, and twenty-fifth embodiments.

In a twenty-seventh embodiment, in a compound, tautomer, deuterated derivative, or pharmaceutically acceptable salt of this disclosure, $R^2$, for each occurrence, is independently selected from Cl and —$CF_3$; and all other variables not specifically defined herein are as defined in any one of the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, and twenty-sixth embodiments.

In a twenty-eighth embodiment, in a compound, tautomer, deuterated derivative, or pharmaceutically acceptable salt of this disclosure, k is an integer selected from 0, 1, and 2; and all other variables not specifically defined herein are as defined in any one of the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, and twenty-seventh embodiments.

In a twenty-ninth embodiment, in a compound, tautomer, deuterated derivative, or pharmaceutically acceptable salt of this disclosure, m is an integer selected from 1 and 2; and all other variables not specifically defined herein are as defined in any one of the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, and twenty-eighth embodiments.

In a thirtieth embodiment, in a compound, tautomer, deuterated derivative, or pharmaceutically acceptable salt of this disclosure, n is O; and all other variables not specifically defined herein are as defined in any one of the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, and twenty-ninth embodiments.

In certain embodiments, the at least one compound of the disclosure is selected from Compounds 1 to 4 depicted in Table 1, a tautomer thereof, a deuterated derivative of the compound or the tautomer, or a pharmaceutically acceptable salt of the foregoing.

TABLE 1

| Compounds 1 to 4 | |
|---|---|
| 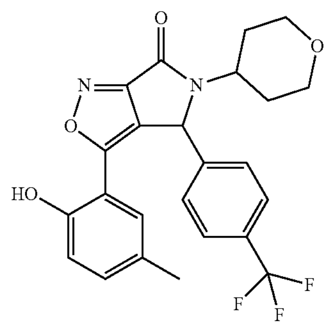 [SMILES: Cc1ccc(O)c(-c2onc3c2C(c2ccc(C(F)(F)F)cc2)N(C2CCOCC2)C3=O)c1] | 1 |
| 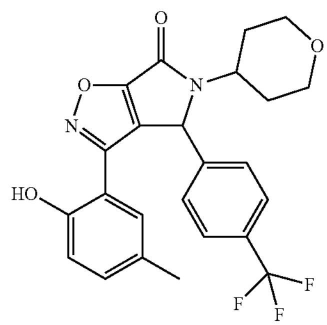 [SMILES: Cc1ccc(O)c(-c2noc3c2C(c2ccc(C(F)(F)F)cc2)N(C2CCOCC2)C3=O)c1] | 2 |
| 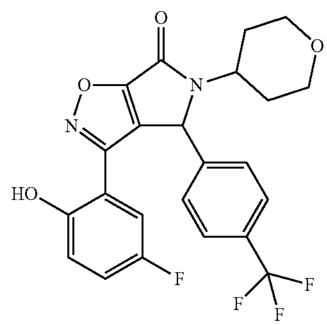 [SMILES: O=C1c2onc(-c3cc(F)ccc3O)c2C(c2ccc(C(F)(F)F)cc2)N1C1CCOCC1] | 3 |
| 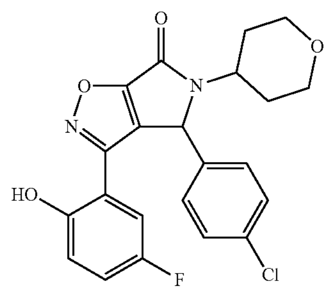 [SMILES: O=C1c2onc(-c3cc(F)ccc3O)c2C(c2ccc(Cl)cc2)N1C1CCOCC1] | 4 |

Another aspect of the disclosure provides pharmaceutical compositions comprising at least one compound selected from a compound of Formulae I, IIa, IIb, III, IV, V, VI, and VII, Compounds 1 to 4, a tautomer thereof, a deuterated derivative of the compound or the tautomer, or a pharmaceutically acceptable salt of the foregoing, or a pharmaceutical composition comprising any of the foregoing, and at least one pharmaceutically acceptable carrier.

In some embodiments, the pharmaceutically acceptable carrier is selected from pharmaceutically acceptable vehicles and pharmaceutically acceptable adjuvants. In some embodiments, the pharmaceutically acceptable carrier is chosen from pharmaceutically acceptable fillers, disintegrants, surfactants, binders, and lubricants.

It will also be appreciated that a pharmaceutical composition of this disclosure can be employed in combination therapies; that is, the pharmaceutical compositions described herein can further include an additional active pharmaceutical agent. Alternatively, a pharmaceutical composition comprising a compound selected from a compound of Formulae I, IIa, IIb, III, IV, V, VI, and VII, Compounds 1 to 4, a tautomer thereof, a deuterated derivative of the compound or the tautomer, or a pharmaceutically acceptable salt of the foregoing, or a pharmaceutical composition comprising any of the foregoing can be administered as a separate composition concurrently with, prior to, or subsequent to, a composition comprising an additional active pharmaceutical agent.

As described above, the pharmaceutical compositions disclosed herein comprise a pharmaceutically acceptable carrier. The pharmaceutically acceptable carrier may be chosen from adjuvants and vehicles. The pharmaceutically acceptable carrier, as used herein, can be chosen, for example, from any and all solvents, diluents, other liquid vehicles, dispersion aids, suspension aids, surface active agents, isotonic agents, thickening agents, emulsifying agents, preservatives, solid binders, and lubricants, which are suited to the particular dosage form desired. Remington: *The Science and Practice of Pharmacy,* 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988 to 1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as sodium lauryl sulfate and magnesium stearate), coloring agents, releasing agents, coating agents, sweetening agents, flavoring agents, perfuming agents, preservatives, and antioxidants.

III. Methods of Treatment and Uses

In another aspect of this disclosure, a compound, tautomer, deuterative derivative, or pharmaceutically acceptable salt as described herein, including a compound of Formulae I, IIa, IIb, III, IV, V, VI, and VII, Compounds 1 to 4, a tautomer thereof, a deuterated derivative of the compound or the tautomer, or a pharmaceutically acceptable salt of the foregoing, or the pharmaceutical composition thereof, is for use in treating a disease, a disorder, or a condition mediated by the signaling of FPR1. In another aspect, disclosed herein is use of a compound, tautomer, deuterative derivative, or pharmaceutically acceptable salt as described herein, including a compound of Formulae I, IIa, IIb, III, IV, V, VI, and VII, Compounds 1 to 4, a tautomer thereof, a deuterated derivative of the compound or the tautomer, or a pharmaceutically acceptable salt of the foregoing, or the pharmaceutical composition thereof, for the manufacture of a medicament for treating a disease, a disorder, or a condition mediated by the signaling of FPR1. In yet another aspect, disclosed herein is a method of treating a disease, a disorder, or a condition mediated by the signaling of FPR1 in a subject, comprising administering a therapeutically effective amount of a compound, tautomer, deuterative derivative, or pharmaceutically acceptable salt as described herein, including a compound of Formulae I, IIa, IIb, III, IV, V, VI, and VII, Compounds 1 to 4, a tautomer thereof, a deuterated derivative of the compound or the tautomer, or a pharmaceutically acceptable salt of the foregoing, or the pharmaceutical composition thereof.

In some embodiments, the disease, the disorder, or the condition is related to the central nervous system (CNS). In some embodiment, the disease, the disorder, or the condition is selected from stroke, dementia, Alzheimer's disease, Parkinson's disease, Picks disease, fronto-temporal dementia, vascular dementia, normal pressure hydrocephalus, epilepsy, seizure disorder, amyotrophic lateral sclerosis (ALS), spinal motor atrophies, Tay-Sach's, Sandoff disease, familial spastic paraplegia, spinocerebellar ataxia (SCA), Friedrich's ataxia, Wilson's disease, Menke's Sx, cerebral autosomal dominant arteriopathy with subcortical infarcts (CADASIL); spinal muscular atrophy, muscular dystrophies, Charcot Marie Tooth diseases, neurofibromatosis, von-Hippel Lindau, Fragile X, spastic paraplesia, tuberous sclerosis, Wardenburg syndrome, dystonias, benign essential tremor, tardive dystonia, tardive dyskinesia, Tourette's syndrome, ataxic syndromes, Shy Drager, Olivopontoicerebellar degeneration, striatonigral degenration, Gullian Barre syndrome, causalgia, complex regional pain syndrome types I and II, diabetic neuropathy, and alcoholic neuropathy, trigeminal neuropathy, trigeminal neuralgia, Menier's syndrome, glossopharangela neuralgia, dysphagia, dysphonia, cranial nerve palsies, myelopethies, traumatic brain injury, traumatic spinal injury, radiation brain injury, multiple sclerosis, post-menengitis syndrome, prion diseases, myelities, radiculitis, diabetes associated with dysproteinemias, transthyretin-induced neuropathies, neuropathy associated with HIV, neuropathy associated with Lyme disease, neuropathy associated with herpes zoster, carpal tunnel syndrome, tarsal tunnel syndrome, amyloid-induced neuropathies, leprous neuropathy, Bell's palsy, compression neuropathies, sarcoidosis-induced neuropathy, polyneuritis cranialis, heavy metal induced neuropathy, transition metal-induced neuropathy, drug-induced neuropathy, axonic brain damage, encephalopathies, chronic fatigue syndrome, and a malignant glioma.

In one embodiment, the disease, the disorder, or the condition is stroke (thrombotic, embolic, thromboembolic, hemorrhagic, venoconstrictive, and venous). In one embodiment, the disease, the disorder, or the condition is traumatic brain injury. In one embodiment, the disease, the disorder, or the condition is a malignant glioma. In one embodiment, the malignant glioma is selected from glioblastoma, anaplastic astrocytoma, anaplastic oligdendroglioma, anaplastic oligoastrocytoma, anaplastic ependymoma, and anaplastic ganglioglioma. In one embodiment, the malignant glioma is glioblastoma.

In another aspect of this disclosure, a compound, tautomer, deuterative derivative, or pharmaceutically acceptable salt as described herein, including a compound of Formulae I, IIa, IIb, III, IV, V, VI, and VII, Compounds 1 to 4, a tautomer thereof, a deuterated derivative of the compound or the tautomer, or a pharmaceutically acceptable salt of the foregoing, or the pharmaceutical composition thereof, is for use in modulating FPR1 activity. In another aspect, disclosed herein is use of a compound, tautomer, deuterative derivative, or pharmaceutically acceptable salt as described herein, including a compound of Formulae I, IIa, IIb, III, IV, V, VI, and VII, Compounds 1 to 4, a tautomer thereof, a deuterated derivative of the compound or the tautomer, or a pharmaceutically acceptable salt of the foregoing, or the pharmaceutical composition thereof, for the manufacture of a medicament for modulating FPR1 activity. In yet another aspect, disclosed herein is a method of modulating FPR1 activity, comprising administering a therapeutically effective amount of a compound, tautomer, deuterative derivative, or pharmaceutically acceptable salt as described herein to a subject, including a compound of Formulae I, IIa, IIb, III, IV, V, VI, and VII, Compounds 1 to 4, a tautomer thereof, a deuterated derivative of the compound or the tautomer, or a pharmaceutically acceptable salt of the foregoing, or the pharmaceutical composition thereof. In yet another aspect, disclosed herein is a method of modulating FPR1 activity, comprising contacting said FPR1 a compound, tautomer, deuterative derivative, or pharmaceutically acceptable salt as described herein to a subject, including a compound of Formulae I, IIa, IIb, III, IV, V, VI, and VII, Compounds 1 to 4, a tautomer thereof, a deuterated derivative of the compound or the tautomer, or a pharmaceutically acceptable salt of the foregoing, or the pharmaceutical composition thereof.

A compound of Formulae I, IIa, IIb, III, IV, V, VI, and VII, Compounds 1 to 4, a tautomer thereof, a deuterated derivative of the compound or the tautomer, or a pharmaceutically acceptable salt of the foregoing, or the pharmaceutical composition thereof may be administered once daily, twice daily, or three times daily, for example, for the treatment of a disease, a disorder, or a condition mediated by the signaling of FPR1.

In some embodiments, 2 mg to 1500 mg or 5 mg to 1000 mg of a compound of Formulae I, IIa, IIb, III, IV, V, VI, and VII, Compounds 1 to 4, a tautomer thereof, a deuterated derivative of the compound or the tautomer, or a pharmaceutically acceptable salt of the foregoing, or the pharmaceutical composition thereof are administered once daily, twice daily, or three times daily.

A compound of Formulae I, IIa, IIb, III, IV, V, VI, and VII, Compounds 1 to 4, a tautomer thereof, a deuterated derivative of the compound or the tautomer, or a pharmaceutically acceptable salt of the foregoing, or the pharmaceutical composition thereof may be administered, for example, by oral, parenteral, sublingual, topical, rectal, nasal, buccal, vaginal, transdermal, patch, pump administration or via an implanted reservoir, and the pharmaceutical compositions would be formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time. Other forms of administration contemplated in this disclosure are as described in International Patent Application Nos. WO 2013/075083, WO 2013/075084, WO 2013/078320, WO 2013/120104, WO 2014/124418, WO 2014/151142, and WO 2015/023915.

Useful dosages or a therapeutically effective amount of a compound or pharmaceutically acceptable salt thereof as described herein can be determined by comparing their in vitro activity and in vivo activity in animal models. Methods for the extrapolation of effective dosages in mice and other animals, to humans are known to the art; for example, see U.S. Pat. No. 4,938,949.

One of ordinary skill in the art would recognize that, when an amount of compound is disclosed, the relevant amount of a pharmaceutically acceptable salt form of the compound is an amount equivalent to the concentration of the free base of the compound. The amounts of the compounds, pharmaceutically acceptable salts, solvates, and deuterated derivatives disclosed herein are based upon the free base form of the reference compound. For example, "1000 mg of at least one compound chosen from compounds of Formula I and pharmaceutically acceptable salts thereof" includes 1000 mg of compound of Formula I) and a concentration of a pharmaceutically acceptable salt of compounds of Formula I equivalent to 1000 mg of compounds of Formula I.

EXAMPLES

In order that the disclosure described herein may be more fully understood, the following examples are disclosed herein. It should be understood that these examples are for illustrative purposes only and are not to be construed as limiting this disclosure in any way.

Example 1. Synthesis of Exemplary Compounds

The compounds of the disclosure may be made according to standard chemical practices or as described herein, including the following synthetic schemes and in the descriptions for preparing a compound selected from compounds of Formulae I, IIa, IIb, III, IV, V, VI, and VII, Compounds 1 to 4, a tautomer thereof, a deuterated derivative of the compound or the tautomer, or a pharmaceutically acceptable salt of the foregoing.

Using Compounds 1 and 2 as representative examples, processes for preparing compounds of Formula I comprise the general reaction steps as described in Scheme 1.

Compounds 1 and 2
Rac-3-(2-hydroxy-5-methylphenyl)-5-(tetrahydro-2H-pyran-4-yl)-4-(4-(trifluoro methyl)phenyl)-4,5-dihydro-6H-pyrrolo[3,4-c]isoxazol-6-one
(Compound 1)
Rac-3-(2-hydroxy-5-methylphenyl)-5-(tetrahydro-2H-pyran-4-yl)-4-(4-(trifluoromethyl)phenyl)-4,5-dihydro-6H-pyrrolo[3,4-d]isoxazol-6-one
(Compound 2)
Scheme 1
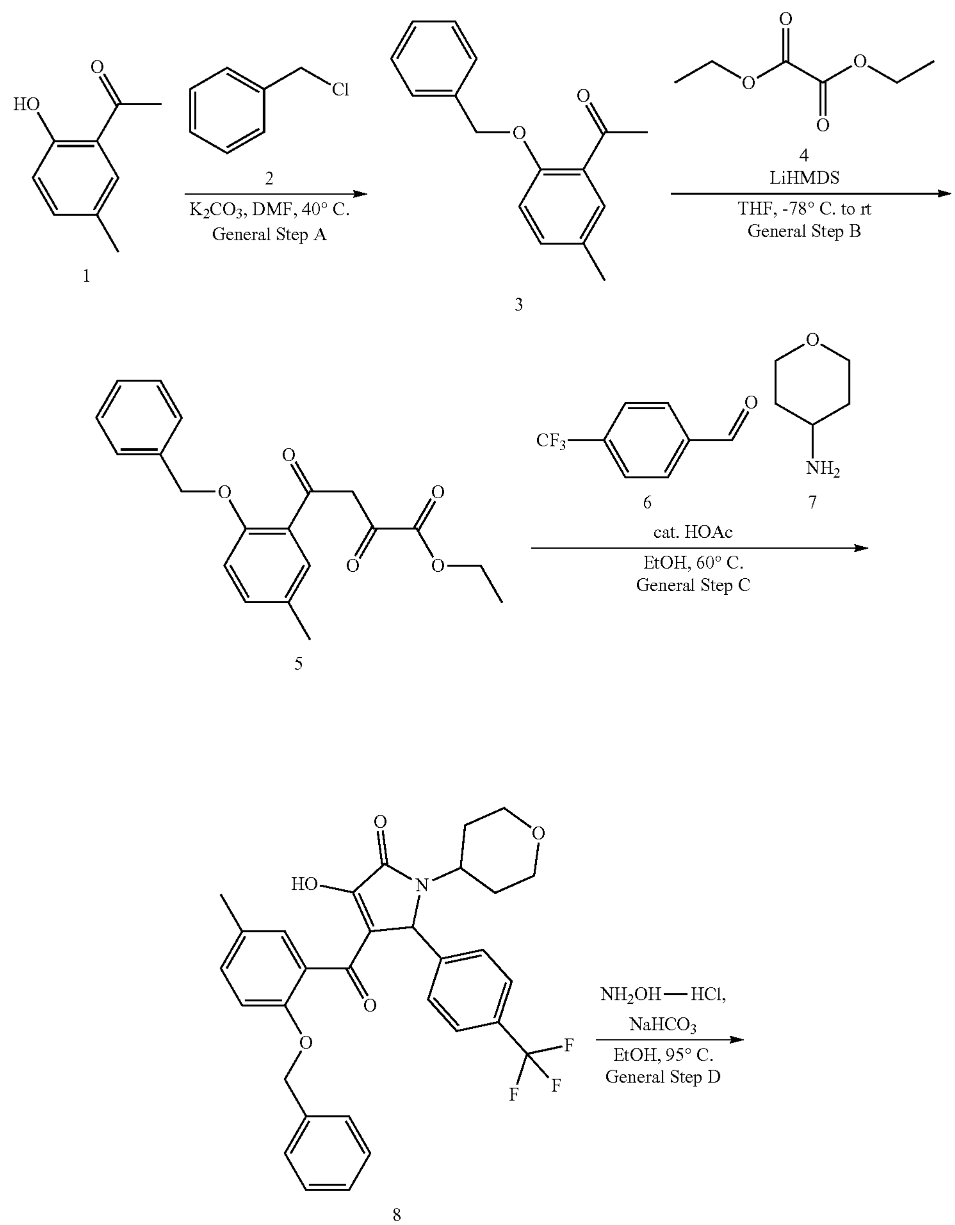

-continued

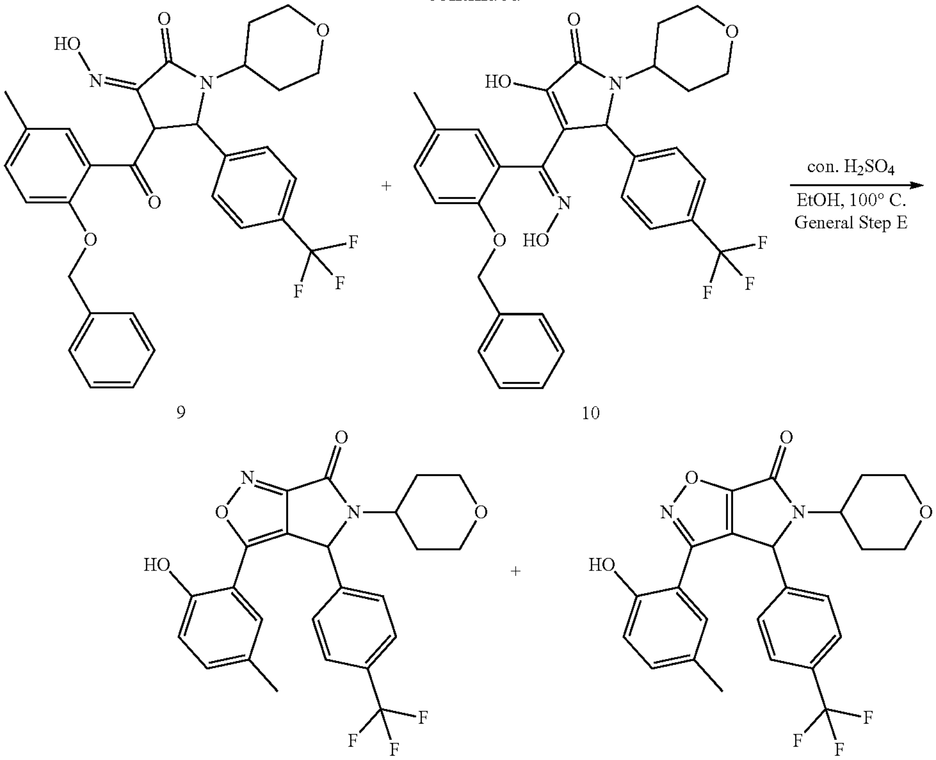

9 10

Compound 1 Compound 2

General Step A: Preparation of 1-(2-(benzyloxy)-5-methylphenyl)ethan-1-one

To a solution of 1-(2-hydroxy-5-methylphenyl)ethenone (4.25 g, 28 mmol) and potassium carbonate or $K_2CO_3$ (7.81 g, 56 mmol) in dimethyl formamide DMF (50 mL) (chloromethyl)benzene (7.81 g, 56 mmol) was added, and the resulting solution was then stirred at 40° C. under nitrogen gas $N_2$ for 16 hrs. To the reaction mixture water (100 mL) was added, and the aqueous solution was then extracted with ethyl acetate or EtOAc (50 mL×3). The combined organic layers were washed with brine (80 mL×2), dried over sodium sulfate or $Na_2SO_4$, and filtered. The filtrate was concentrated under vacuum to dryness to give the desired product 1-(2-(benzyloxy)-5-methylphenyl)ethan-1-one as brown oil (6 g, 88%). Mass (m/z): 240.9 $[M+H]^+$.

General Step B: Preparation of ethyl 4-(2-(benzyloxy)-5-methylphenyl)-2,4-dioxobutanoate To a solution of 1-(2-(benzyloxy)-5-methylphenyl)ethan-1-one (5 g, 20.8 mmol) and diethyl oxalate (3.04 g, 20.8 mmol) in tetrahydrofuran or THE (80 mL), lithium bis (trimethylsilyl)amide LiHMDS (1.0 μM in THF, 20.8 mL, 20.8 mmol) was added dropwise at −78° C. under $N_2$. The reaction mixture was warmed to room temperature (rt) slowly, and stirred at room temperature for 1 hr. The reaction was quenched with water (150 mL), and the aqueous solution was then extracted with EtOAc (100 mL×3). The combined organic layers were washed with brine (100 mL×2), dried over $Na_2SO_4$, and filtered. The filtrate was concentrated under vacuum, and the residue was purified by flash column chromatography (petrol ether:ethylacetate or PE:EA=2:1, then dichloromethane:methanol or DCM: MeOH=20:1) to give the product ethyl 4-(2-(benzyloxy)-5-methylphenyl)-2,4-dioxobutanoate as yellow solid (7 g, 90%). Mass (m/z): 340.9 $[M+H]^+$.

General Step C: Preparation of rac-4-(2-(benzyloxy)-5-methylbenzoyl)-3-hydroxy-1-(tetrahydro-2H-pyran-4-yl)-5-(4-(trifluoromethyl)phenyl)-1,5-dihydro-2H- pyrrol-2-one To a solution of 4-(trifluoromethyl)benzaldehyde (1.13 g, 6.49 mmol) and tetrahydro-2H-pyran-4-amine (656 mg, 6.49 mmol) in EtOH (15 mL), catalytic acetic acid or HOAc (two drops) was added under $N_2$, and the reaction mixture was then stirred at 60° C. for 3.5 hrs. The reaction mixture was cooled to room temperature before the addition of ethyl 4-(2-(benzyloxy)-5-methylphenyl)-2,4-dioxobutanoate (2 g, 5.9 mmol). The reaction mixture was further stirred at 60° C. under $N_2$ for 16 hrs. Solid was precipitated, collected by filtration, and dried to give the product rac-4-(2-(benzyloxy)-5-methylbenzoyl)-3-hydroxy-1-(tetrahydro-2H-pyran-4-yl)-5-(4-(trifluoromethyl)phenyl)-1,5-dihydro-2H-pyrrol-2-one as white solid (1.3 g, 40%). Mass (m/z): 551.7 $[M+H]^+$.

General Steps D and E: Preparation of rac-3-(2-hydroxy-5-methylphenyl)-5-(tetrahydro-2H-pyran-4-yl)-4-(4-(trifluoromethyl)phenyl)-4,5-dihydro-6H-pyrrolo[3,4-c]isoxazol-6-one (Compound 1) and rac-3-(2-hydroxy-5-methylphenyl)-5-(tetrahydro-2H-pyran-4-yl)-4-(4-(trifluoromethyl)phenyl)-4,5-dihydro-6H-pyrrolo[3,4-d]isoxazol-6-one (Compound 2)

A mixture of rac-4-(2-(benzyloxy)-5-methylbenzoyl)-3-hydroxy-1-(tetrahydro-2H-pyran-4-yl)-5-(4-(trifluoromethyl)phenyl)-1,5-dihydro-2H-pyrrol-2-one (500 mg, 0.91 mmol), hydroxylamine hydrochloride (125 mg, 1.82 mmol) and sodium bicarbonate or $NaHCO_3$ (153 mg, 1.82 mmol) in EtOH (20 mL) was stirred at 95° C. under nitrogen gas or $N_2$ for 16 hrs, and then cooled down to room temperature. Concentrated sulfuric acid or $H_2SO_4$ (5 mL) was added into the reaction mixture dropwise, and the resulting solution was further stirred at 100° C. under $N_2$ for 5 hrs. The solution was cooled down to room temperature, and then diluted with water (50 mL). The aqueous solution was extracted with EtOAc (30 mL×3). The combined organic layers were washed with brine (20 mL×2), dried over $Na_2SO_4$, and filtered. The filtrate was concentrated under vacuum, and the residue was purified by prep-HPLC (Gemini-$C_{18}$ $_{150\times21.2}$ mm, Sum; ACN-$H_2O$ (0.1% FA), 55-60%) to give the products rac-3-(2-hydroxy-5-methylphenyl)-5-(tetrahydro-2H-pyran-4-yl)-4-(4-(trifluoromethyl)phenyl)-4,5-dihydro-6H-pyrrolo[3,4-c]isoxazol-6-one (Compound 1) (48 mg, 12%, white solid) and rac-3-(2-hydroxy-5-methylphenyl)-5-(tetrahydro-2H-pyran-4-yl)-4-(4-(trifluoromethyl)phenyl)-4,5-dihydro-6H-pyrrolo[3,4-d]isoxazol-6-one (Compound 2) (8 mg, 2%, white solid). rac-3-(2-hydroxy-5-methylphenyl)-5-(tetrahydro-2H-pyran-4-yl)-4-(4-(trifluoromethyl)phenyl)-4,5-dihydro-6H-pyrrolo[3,4-c]isoxazol-6-one (Compound 1): Mass (m/z): 458.7 $[M+H]^+$. rac-3-(2-hydroxy-5-methylphenyl)-5-(tetrahydro-2H-pyran-4-yl)-4-(4-(trifluoromethyl)phenyl)-4,5-dihydro-6H-pyrrolo[3,4-d]isoxazol-6-one (Compound 2): Mass (m/z): 458.8 $[M+H]^+$.

Processes for preparing Compounds 3 and 4 are described as follows.

Compounds 3 and 4

Rac-3-(5-fluoro-2-hydroxyphenyl)-5-(tetrahydro-2H-pyran-4-yl)-4-(4-(trifluoromethyl)phenyl)-4,5-dihydro-6H-pyrrolo[3,4-d]isoxazol-6-one (Compound 3)

Scheme 2

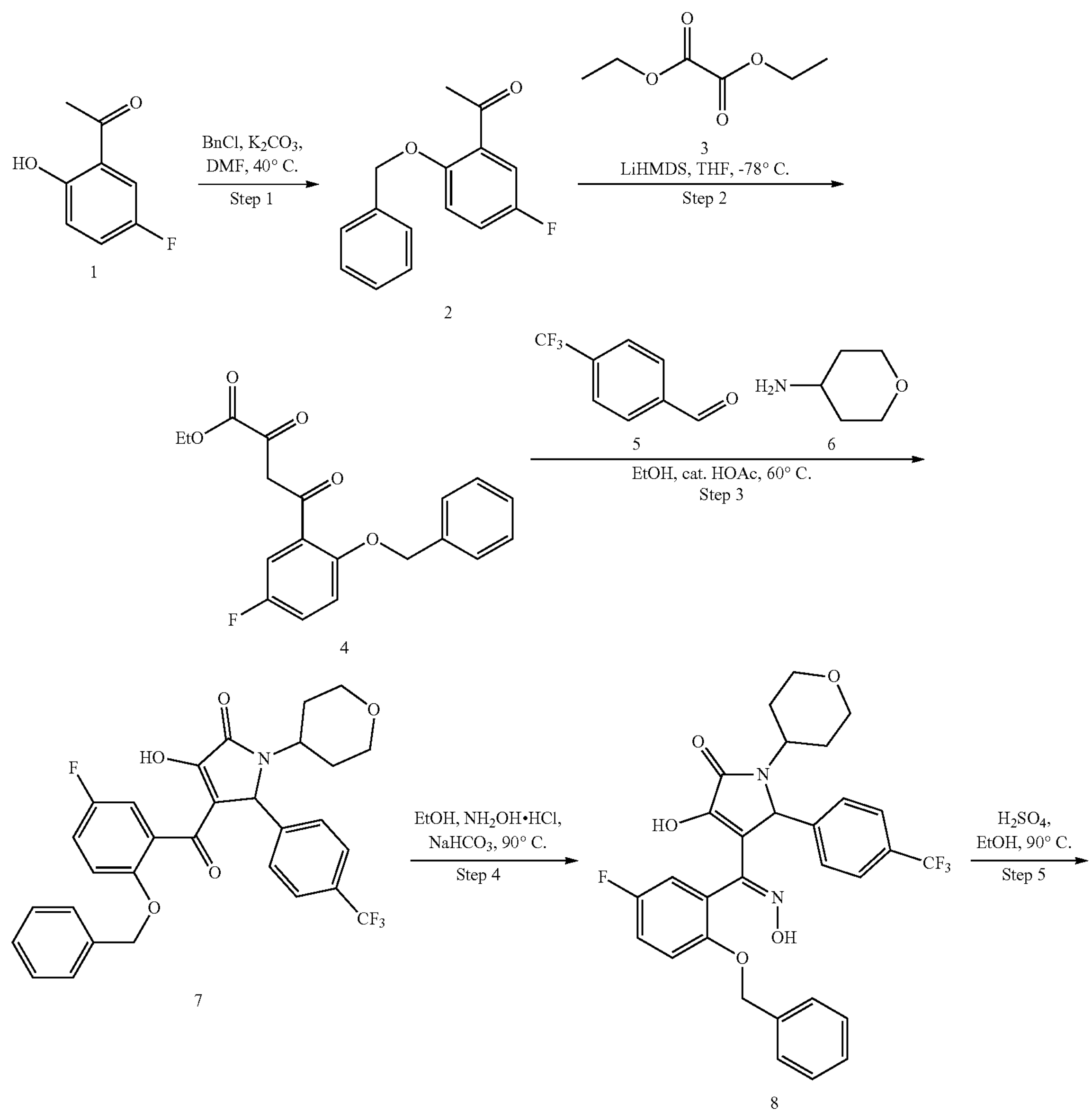

-continued

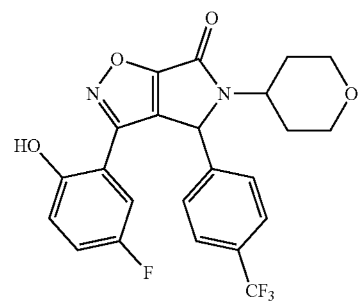

Compound 3

Step 1. Following General Step A, 1-(2-(benzyloxy)-5-fluorophenyl)ethan-1-one (2) was prepared as yellow oil (6.4 g, 100%).

Step 2. Following General Step B, ethyl 4-(2-(benzyloxy)-5-fluorophenyl)-2,4-dioxobutanoate (4) was prepared as yellow oil (7.0 g, 98%, crude).

Step 3. Following General Step C, rac-4-(2-(benzyloxy)-5-fluorobenzoyl)-3-hydroxy-1-(tetrahydro-2H-pyran-4-yl)-5-(4-(trifluoromethyl)phenyl)-1,5-dihydro-2H-pyrrol-2-one (7) was prepared as colorless oil (400 mg, 43%, crude). Mass (m/z): 556.1 [M+H]$^+$.

Steps 4 and 5. Following General Steps D and E, rac-3-(5-fluoro-2-hydroxyphenyl)-5-(tetrahydro-2H-pyran-4-yl)-4-(4-(trifluoromethyl)phenyl)-4,5-dihydro-6H-pyrrolo[3,4-d]isoxazol-6-one (Compound 3) was prepared as white solid (5 mg, 2%). Mass (m/z): 463.0 [M+H]$^+$.

Compound 4

Rac-4-(4-chlorophenyl)-3-(5-fluoro-2-hydroxyphenyl)-5-(tetrahydro-2H-pyran-4-yl)-4,5-dihydro-6H-pyrrolo[3,4-d]isoxazol-6-one (Compound 6)

Scheme 3

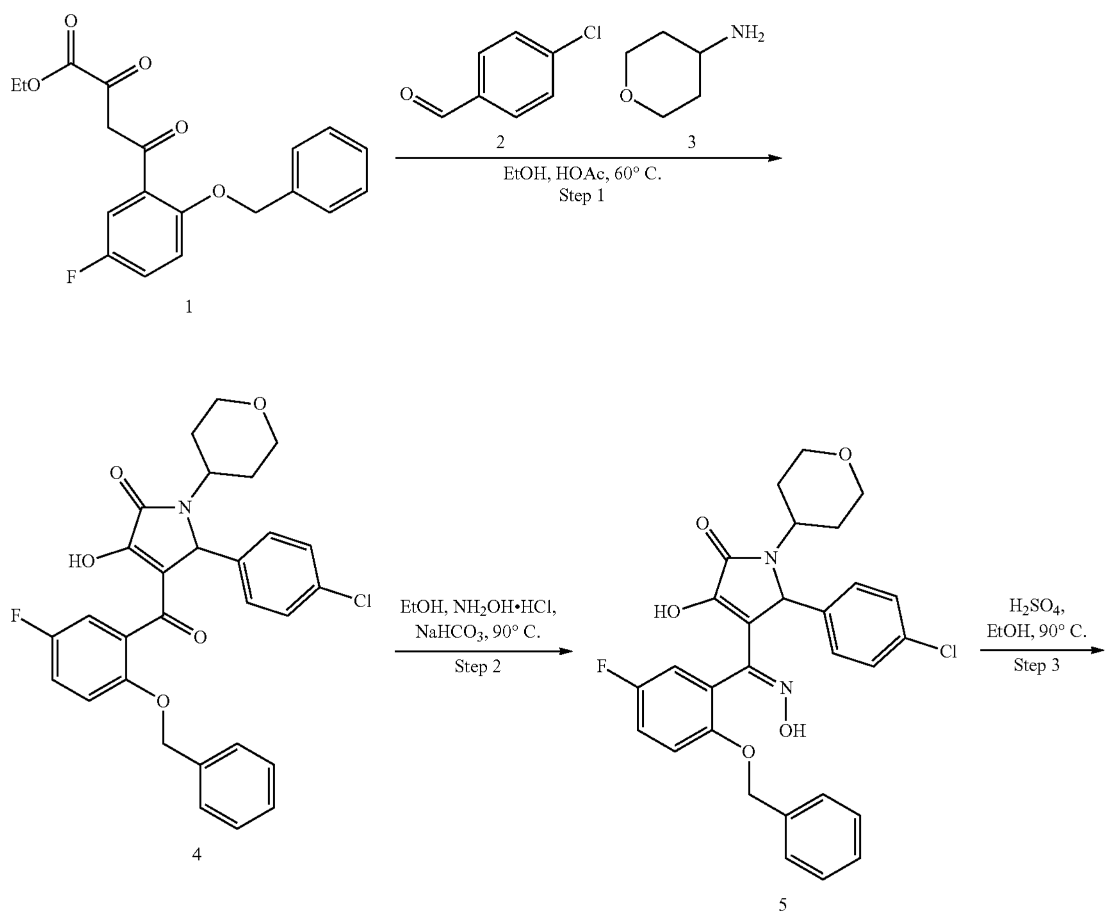

-continued

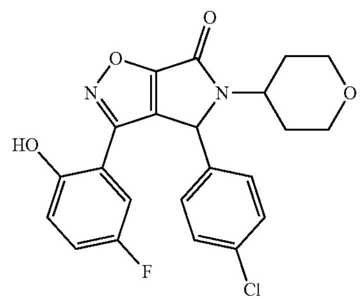

Compound 4

Step 1. Following General Step C, rac-4-(2-(benzyloxy)-5-fluorobenzoyl)-5-(4-chlorophenyl)-3-hydroxy-1-(tetrahydro-2H-pyran-4-yl)-1,5-dihydro-2H-pyrrol-2-one (4) was prepared as colorless oil (300 mg, 35%, crude). Mass (m/z): 522.0 $[M+H]^+$.

Steps 2 and 3. Following General Steps D and E, rac-4-(4-chlorophenyl)-3-(5-fluoro-2-hydroxyphenyl)-5-(tetrahydro-2H-pyran-4-yl)-4,5-dihydro-6H-pyrrolo[3,4-d]isoxazol-6-one (Compound 4) was prepared as white solid (5 mg, 2%). Mass (m/z): 429.0 $[M+H]^+$.

Example 2. In Vitro Assay for Detecting and Measuring Modulation of FPR1-Mediated Calcium Signaling of Compounds 1 to 4

The effects of the compounds of this disclosure on regulating the FPR1-mediated cell signaling were measured by monitoring the cellular calcium level change, as illustrated by the exemplary examples in Table 2. The dose responses of the illustrated examples are reported categorically using the following ranking criteria: *($IC_{50}$≤100 nM); ($IC_{50}$≥100 to ≤1000 nM); *($IC_{50}$≥1000 to ≤10,000 nM); N.D.—not detected.

Expression of Human or Mouse FPR1 in 293T Cells

The coding DNA sequence (CDS) of human FPR1 (NM_001193306) and mouse FPR1 (NM_013521) were cloned and inserted to the lentivirus vector GV367 from GeneChem (Shanghai, China) under the conduction of pCMV promoter. 293T cells were cultured in H-DMEM supplemented with 10% FBS and 1% penicillin-streptomycin (PS) at 37° C. in 5% CO2 Incubator. 293T cells were transfected with lentivirus vector GV367 containing the CDS of human or mouse FPR1 for 24 h and then cultured with complete medium for another 48 h. At 72 h after transfected, cells were passaged, and 5 μg/ml puromycin was added to screen FPR1-transfected 293T cells. The overexpression of human or mouse FPR1 in 293 T cells were detected by immunostaining with anti-mouse or human FPR1 antibodies (Biolegend or Antibody Online).

Measurement of fMLP-FPR1 Mediated Intracellular Calcium Concentration in 293T Cells Cultured hFPR1 or mFPR1 overexpressing 293T cells were labeled with 1 μM INDO-1 AM calcium sensor dye (eBioscience) for 30 min at 37° C. After washed with 1×PBS, cells were resuspended with H-DMEM containing 3% FBS, and were maintained on ice prior to the measurement of intracellular calcium concentration. To measure the inhibitory potency of designed potential FPR1 antagonists, hFPR1 or mFPR1 overexpressing 293T cells were incubated with the compound for 10 min at room temperature. The cytoplasmic calcium levels were then measured by FACS Aria III at 37° C. prior to and after the stimulation of fMLP. We defined the immunofluorescence intensity of indo-1 AM before adding fMLP as the basal value, and the intensity at the peak immunofluorescence reduction after adding fMLP as minimum value for each sample. The change of intracellular calcium was calculated as follow: (basal value-minimum value)/basal value×100%. The $IC_{50}$ of each compound in inhibiting fMLP-FPR1 mediated intracellular calcium concentration in 293T cells were automatically calculated with Prism software (GraphPad) after inputting a series of change of intracellular calcium at multiple concentration gradients (from 0 nM to 100 PM).

TABLE 2

Potency of exemplary compounds in calcium signaling assay

| Compound No. | $IC_{50}$ (nM) |
|---|---|
| 1 | * |
| 2 | ** |
| 3 | N.D. |
| 4 | N.D. |

Example 3. In Vivo Pre-Clinical Efficacy in Intracerebral Hemorrhage (ICH) Mouse Model The efficacy of the compounds of this disclosure in protecting brain damage and improving brain functions after stroke and/or brain injury are demonstrated in the experiments described below using Compound 1 as a representative compound in the experimental ICH mouse model.

Preparation of the Experimental Mouse ICH Model

The intracerebral hemorrhage (ICH) model in mice was used to illustrate the protective benefits of the compounds of this disclosure, and FIG. 1 depicts the procedure in preparing this model. ICH was induced in C57 B/L6 male mice by the injection of an autologous blood or collagenase as previously described (Lauer et al., *Circulation* 124:1654-1662 (2011); Rynkowski et al., *Nat. Protoc.* 3:122-128 (2008)). Mice were anesthetized using isoflurane inhalation and fixed on a stereotactic frame. A burr hole was drilled on the right side of the skull at 2.3 mm lateral to the midline and 0.5 mm anterior to the bregma. For the autologous blood model, 30 μl of non-heparinized blood was withdrawn from the angular vein. The first 5 μl blood was injected at a depth of 3 mm beneath the hole, and the rest 25 μl blood were injected at 3.7 mm beneath the hole with a rate of 1 μl/min. In the collagenase model, 0.038 U of the bacterial collagenase (in 0.5 μl saline) was infused to the striatum (0.5 mm anterior, 2.3 mm right lateral, and 3.5 mm deep relative to bregma) at a speed of 0.5 μl/min. Mice on the sham control were injected with an equal volume of saline. Throughout the procedure, the body temperature was maintained at 37° C. with a homeothermic blanket. After the surgery, mice were under observation with free access to food and water. Compound was dissolved in DMSO and dosed at 5 mg/kg twice a day via intraperitoneal injection, at the dosing volume of 1 ml/kg body weight. The first dose was administrated at 1 h after the ICH onset.

Neurological Function Assessment

The neurological function assessment was performed by investigators who were blinded to the two treatment groups. The modified Neurological Severity Score (mNSS), corner-turning test, and rotarod test were conducted to evaluate the neuro-deficits of the ICH mice at defined time points as described (Li et al., *Proc. Nat. Acad. Sci. USA* 114:E396-E405 (2017)). mice were evaluated for motor function (muscle and abnormal movement), sensory (visual, tactile, and proprioceptive), and reflexes (pinna, corneal, startle reflexes). The range of scores is from 0 to 18 and defined as follows: Severe injury (13 to 18); Moderate injury (7 to 12); Mild injury (1 to 6). The corner-turning test was used to evaluate the sensorimotor damage to quantify the turning preference (right or left) upon approaching a 300 corner. Lesioned mice typically have a turning preference which is correlated to the extent of striatal injury. Each mouse repeated the procedure for 10 times with an interval of at least 30 seconds between trials. The percentage of ipsilateral turns was then calculated. The rotarod test was used to evaluate the motor coordination and balance. Mice were trained for one week prior to ICH induction. At the specified time points after ICH, mice were placed on a rotarod apparatus. The rotating rod is of 3 cm diameter with a non-slippery surface. The rod was 30 cm in length and placed at height of 20 cm from the base. Each mouse was placed on the rod at a speed of 4 rpm (rotations per minute) which accelerates over the course of 5 min to 40 rpm. The duration of each mouse on the rod was recorded. Each mouse was tested in 3 consecutive trials with an interval of 15 minutes in between. The results were reported as the average of the three trials.

Edema Reduction in MRI Neuroimaging

The total lesion volume was measured on the 7T small-animal MRI scanner (Bruker, Corp., USA) as described (Li et al., 2017). The T2-weighted water imaging was recorded with following parameters (repetition time (TR)=4500 ms, echo time (TE)=65.5 ms, field of view (FOV)=28×28 $mm^2$, image matrix=256×256, at 0.5-mm slice thickness). Susceptibility weighted imaging (SWI) was used to measure hematoma. The setup parameters were as follows: TR=30 ms and TE=10 ms, flip angle=25°, FOV=32×32×16 $mm^3$, image matrix=256×256. The volumes were manually outlined and calculated by multiplying the sum of the volume by the distance between sections (0.5 mm) using MIPAV software. PHE volumes were calculated as total lesion volume minus hematoma volume. MRI data were analyzed by two investigators blinded to experimental groups.

Brain Water Content Assessment

Brain water content was measured at day 1 after ICH. Briefly, without perfusion, brain tissue was removed and divided into three parts: the ipsilateral hemisphere, contralateral hemisphere, and cerebellum. The brain tissues were weighed for wet weights, and then dried for 24 hours at 100° C. for dry weights. The following formula was used to calculate the brain water content: (wet weight-dry weight)/wet weight×100%.

Infiltrating Cell Measurement by Flow Cytometry

Single cell suspension of brain tissues was prepared and stained with fluorochrome-conjugated antibodies. Brain tissues were digested with 1% collagenase (Sigma-Aldrich) at 37° C. for 30 min, and then myelin sheath was removed by density gradient centrifugation in 30% percoll (Sigma-Aldrich) at 700 rpm for 10 min. For neutrophils staining, cells were incubated with anti-mouse CD45 (Cat #103108; RRID: AB_312973, Biolegend, 1:100), anti-mouse Ly-6G (Cat #127616; RRID: AB_1877271, Biolegend, 1:100), anti-mouse CD11b (Cat #553311; RRID: AB_394775, BD Biosciences, 1:100) at 4° C. for 30 min following their instruction. Flow cytometric measurements were performed on a FACS Aria III (BD Bioscience) and analyzed using Flowjo 7.6 software (Informer Technologies, Ashland, OR, USA).

One skilled in the art will readily recognize from the disclosure and claims, that various changes, modifications and variations can be made therein without departing from the spirit and scope of the disclosure as defined in the following claims.

The invention claimed is:

1. A compound of the following structural formula IIa:

Formula IIa

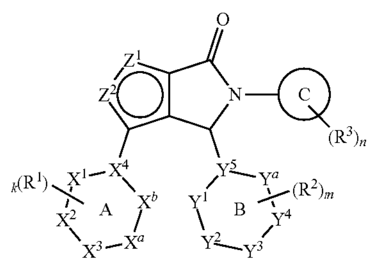

a tautomer thereof, a deuterated derivative of the compound or the tautomer, or a pharmaceutically acceptable salt of the foregoing, wherein:

$Z^1$ is O and $Z^2$ is N, or $Z^1$ is N and $Z^2$ is O;

Ring A is an aromatic or non-aromatic ring, wherein:

$X^a$ and $X^b$ are each independently C, N, or a bond; and $X^1$, $X^2$, $X^3$, and $X^4$ are each independently C or N;

Ring B is an aromatic or non-aromatic ring, wherein:

$Y^a$ is C, N, or a bond; and $Y^1$, $Y^2$, $Y^3$, $Y^4$, and $Y^5$ are each independently C or N;

Ring C is selected from $C_3$-$C_{12}$ carbocyclyl, 3 to 12-membered heterocyclyl, phenyl, and 5 to 10-membered heteroaryl;

$R^1$, $R^2$, and $R^3$, for each occurrence, is independently selected from halogen, cyano, $C_1$-$C_6$ alkyl, $C_2$-$C_6$ alkenyl, $C_1$-$C_6$ alkoxy, —C(═O)($C_1$-$C_6$ alkyl), (C(═O)$NR^hR^i$, —$NR^hR^i$, —$NR^hC$(═O)$R^k$, —$NR^hC$(═O)$OR^k$, —$NR^hC$(═O)$NR^iR^j$, —$NR^hS$(═O)$_pR^k$, —$OR^k$, —OC(═O)$R^k$, —OC(═O)$OR^k$, —OC(═O)$NR^hR^i$, —S(═O)$_pR^k$, —S(═O)$_pNR^hR^i$, $C_3$-$C_{12}$ carbocyclyl, 3 to 12-membered heterocyclyl, phenyl, and 5 to 10-membered heteroaryl; wherein:

the $C_1$-$C_6$ alkyl, the $C_2$-$C_6$ alkenyl, and the $C_1$-$C_6$ alkoxy of any one of $R^1$, $R^2$, and $R^3$ and the $C_1$-$C_6$ alkyl of —C(═O)($C_1$-$C_6$ alkyl) are each optionally substituted with 1 to 3 groups selected from halogen, cyano, —C(═O)$R^k$, —C(═O)$OR^k$, —C(═O)$NR^hR^i$, —$NR^hR^i$, —$NR^hC$(═O)$R^k$, —$NR^hC$(═O)$OR^k$, —$NR^hC$(═O)$NR^iR^j$, —$NR^hs$ $(=O)_pR^k$, $-OR_k$, $-OC(=O)R^k$, $-OC(=O)OR^k$, $-OC(=O)NR^hR^i$, $-S(=O)_pR^k$, $-S(=O)_pNR^hR^i$, and $C_3$-$C_6$ cycloalkyl;

the $C_3$-$C_{12}$ carbocyclyl, the 3 to 12-membered heterocyclyl, the phenyl, the 5 to 10-membered heteroaryl of any one of $R^1$, $R^2$, and $R^3$ are each optionally substituted with 1 to 3 groups selected from halogen, cyano, $C_1$-$C_4$ alkyl, $-NR^hR^i$, and $-OR^k$;

$R^h$, $R^i$, and $R^j$, for each occurrence, are each independently selected from hydrogen, $C_1$-$C_4$ alkyl, and $C_3$-$C_6$ cycloalkyl; wherein:

the $C_1$-$C_4$ alkyl of any one of $R^h$, $R^i$, and $R^j$ is optionally substituted with 1 to 3 groups selected from halogen, cyano, and —OH;

$R^k$, for each occurrence, are each independently selected from hydrogen, $C_1$-$C_4$ alkyl, and $C_3$-$C_6$ cycloalkyl; wherein:

the $C_1$-$C_4$ alkyl of any one of $R^h$, $R^i$, and $R^i$ is optionally substituted with 1 to 3 groups selected from halogen, cyano, and —OH;

k and m are each independently an integer selected from 0, 1, 2, 3, 4, 5, and 6;

n is an integer selected from 0, 1, 2, 3, 4, and 5; and p is an integer selected from 1 and 2.

2. The compound according to claim 1, wherein the compound is of the following structural formula III:

Formula III

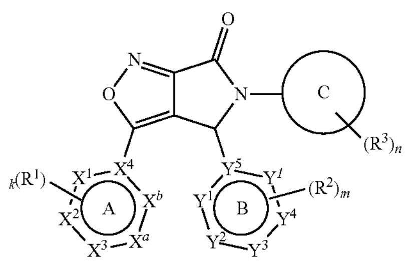

a tautomer thereof, a deuterated derivative of the compound or the tautomer, or a pharmaceutically acceptable salt of the foregoing, wherein:

Ring A and Ring B are each an aromatic ring.

3. The compound according to claim 1, wherein the compound is of the following structural formula IV:

Formula IV

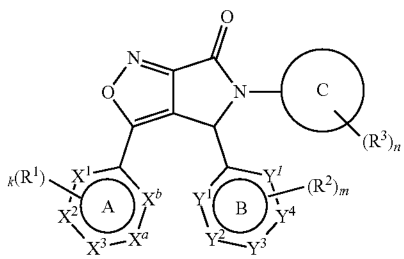

a tautomer thereof, a deuterated derivative of the compound or the tautomer, or a pharmaceutically acceptable salt of the foregoing, wherein:

no more than 3 of $X^a$, $X^b$, $X^1$, $X^2$, and $X^3$ are N; and no more than 3 of $Y^a$, $Y^1$, $Y^2$, $Y^3$, and $Y^4$ are N.

4. The compound, tautomer, deuterated derivative, or pharmaceutically acceptable salt according to claim 1, wherein:

no more than 2 of $X^a$, $X^b$, $X^1$, $X^2$, and $X^3$ are N; and no more than 2 of $Y^a$, $Y^1$, $Y^2$, $Y^3$, and $Y^4$ are N.

5. The compound, tautomer, deuterated derivative, or pharmaceutically acceptable salt according to claim 1, wherein:

$X^a$ and $X^b$ are each C or N; and $Y^a$ is C or N.

6. The compound, tautomer, deuterated derivative, or pharmaceutically acceptable salt according to claim 1, wherein Ring A is pyridinyl or pyrimidinyl substituted with k groups of $R^1$.

7. The compound according to claim 1, wherein the compound is of the following structural formula V:

Formula V

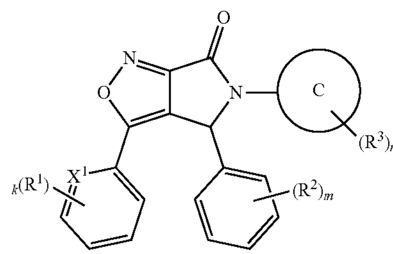

a tautomer thereof, a deuterated derivative of the compound or the tautomer, or a pharmaceutically acceptable salt of the foregoing, wherein $X^1$ is C or N.

8. The compound according to claim 1, wherein the compound is of the following structural formula VI:

Formula VI

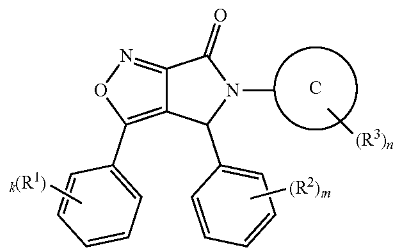

a tautomer thereof, a deuterated derivative of the compound or the tautomer, or a pharmaceutically acceptable salt of the foregoing.

9. The compound, tautomer, deuterated derivative, or pharmaceutically acceptable salt according to claim 1, wherein Ring C is $C_5$-$C_6$ cycloalkyl or 5- to 6-membered heterocyclyl substituted with n groups of $R^3$, wherein the 5- to 6-membered heterocyclyl optionally contains 1 or 2 heteroatoms selected from O and N.

10. The compound, tautomer, deuterated derivative, or pharmaceutically acceptable salt according to claim 1, wherein Ring C is cyclohexyl or 6-membered heterocyclyl with n groups of $R^3$, further wherein the 6-membered heterocyclyl contains 1 or 2 heteroatoms selected from O and N.

11. The compound, tautomer, deuterated derivative, or pharmaceutically acceptable salt according to claim 1, wherein Ring C is tetrahydro-2H-pyranyl substituted with n groups of $R^3$.

12. The compound according to claim 1, wherein the compound is of the following structural formula VII:

Formula VII

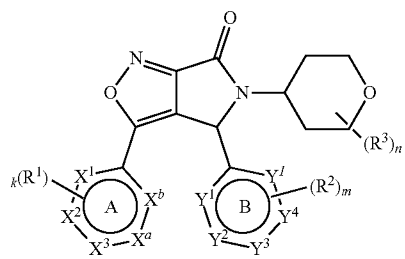

a tautomer thereof, a deuterated derivative of the compound or the tautomer, or a pharmaceutically acceptable salt of the foregoing, wherein:

Ring A and Ring B are each an aromatic ring;

no more than 3 of $X^a$, $X^b$, $X^1$, $X^2$, and $X^3$ are N; and no more than 3 of $Y^a$, $Y^1$, $Y^2$, $Y^3$, and $Y^4$ are N.

13. The compound, tautomer, deuterated derivative, or pharmaceutically acceptable salt according to claim 12, wherein:

no more than 2 of $X^a$, $X^b$, $X^1$, $X^2$, and $X^3$ are N; and no more than 2 of $Y^a$, $Y^1$, $Y^2$, $Y^3$, and $Y^4$ are N.

14. The compound, tautomer, deuterated derivative, or pharmaceutically acceptable salt according to any one of claim 12, wherein:

$X^a$ and $X^b$ are each C or N; and $Y^a$ is C or N.

15. The compound, tautomer, deuterated derivative, or pharmaceutically acceptable salt according to claim 12, wherein Ring A is pyridinyl or pyrimidinyl substituted with k groups of $R^1$.

16. The compound, tautomer, deuterated derivative, prordrug, or pharmaceutically acceptable salt according to claim 1, wherein Ring B is phenyl substituted with m groups of $R^2$.

17. The compound, tautomer, deuterated derivative, or pharmaceutically acceptable salt according to claim 1, wherein $R^1$, $R^2$, and $R^3$, for each occurrence, is independently selected from halogen, cyano, $C_1$-$C_6$ alkyl, $C_1$-$C_6$ alkoxy, —C(═O)($C_1$-$C_6$ alkyl), —C(═O)$NR^hR^i$, —$NR^hR^i$, —$OR^k$, —S(═O)$_2R^k$, —S(═O)$_2NR^hR^i$, $C_3$-$C_6$ cycloalkyl, 5 to 6-membered heterocyclyl, phenyl, and 5 to 6-membered heteroaryl; wherein:

the $C_1$-$C_6$ alkyl and the $C_1$-$C_6$ alkoxy of any one of $R^1$, $R^2$, and $R^3$ and the $C_1$-$C_6$ alkyl of —C(═O)($C_1$-$C_6$ alkyl) are each optionally substituted with 1 to 3 groups selected from halogen, cyano, C(═O)$OR^k$, and —$OR^k$;

the $C_3$-$C_6$ cycloalkyl, the 5 to 6-membered heterocyclyl, the phenyl, and the 5 to 6-membered heteroaryl of any one of $R^1$, $R^2$, and $R^3$ are each optionally substituted with 1 to 3 groups selected from halogen, cyano, $C_1$-$C_4$ alkyl, and —$OR^k$;

$R^h$ and $R^i$, for each occurrence, are each independently selected from hydrogen and $C_1$-$C_4$ alkyl; wherein:

the $C_1$-$C_4$ alkyl of any one of $R^h$ and $R^i$ is optionally substituted with 1 to 3 groups selected from halogen, cyano, and —OH; and $R^k$, for each occurrence, are each independently selected from hydrogen and $C_1$-$C_4$ alkyl; wherein:

the $C_1$-$C_4$ alkyl of any one of $R^h$ and $R^i$ is optionally substituted with 1 to 3 groups selected from halogen, cyano, and —OH.

18. The compound, tautomer, deuterated derivative, or pharmaceutically acceptable salt according to claim 1, wherein $R^1$, $R^2$, and $R^3$, for each occurrence, is independently selected from halogen, cyano, $C_1$-$C_4$ alkyl, $C_1$-$C_4$ alkoxy, —C(═O)($C_1$-$C_4$ alkyl), —C(═O)$NR^hR^i$, —$NR^hR^i$, and —$OR^k$; wherein:

the $C_1$-$C_4$ alkyl and the $C_1$-$C_4$ alkoxy of any one of $R^1$, $R^2$, and $R^3$ and the $C_1$-$C_4$ alkyl of —C(═O)($C_1$-$C_4$ alkyl) are each optionally substituted is optionally substituted with 1 to 3 groups selected from halogen, cyano, and —$OR^k$;

$R^h$ and $R^i$, for each occurrence, are each independently selected from hydrogen and $C_1$-$C_2$ alkyl; and $R^k$, for each occurrence, are each independently selected from hydrogen and $C_1$-$C_2$ alkyl.

19. The compound, tautomer, deuterated derivative, or pharmaceutically acceptable salt according to claim 1, wherein $R^1$, $R^2$, and $R^3$, for each occurrence, is independently selected from halogen, $C_1$-$C_4$ alkyl, $C_1$-$C_4$ alkoxy, —C(═O)($C_1$-$C_4$ alkyl), and —$OR^k$; wherein:

the $C_1$-$C_4$ alkyl of any one of $R^1$, $R^2$, and $R^3$ is optionally substituted is optionally substituted with 1 to 3 groups of halogen; and $R^k$, for each occurrence, are each independently selected from hydrogen and $C_1$-$C_2$ alkyl.

20. The compound, tautomer, deuterated derivative, or pharmaceutically acceptable salt according to claim 1, wherein $R^1$, for each occurrence, is independently selected from F, Cl, Br, $C_1$-$C_2$ alkyl, and —$OR^k$; wherein:

the $C_1$-$C_2$ alkyl of $R^1$ is optionally substituted is optionally substituted with 1 to 3 groups of halogen; and $R^k$, for each occurrence, are each independently selected from hydrogen and $C_1$-$C_2$ alkyl.

21. The compound, tautomer, deuterated derivative, or pharmaceutically acceptable salt according to claim 1, wherein $R^1$, for each occurrence, is independently selected from F, —$CH_3$, and —OH.

22. The compound, tautomer, deuterated derivative, or pharmaceutically acceptable salt according to claim 1, wherein $R^2$, for each occurrence, is independently selected from F, Cl, Br, and $C_1$-$C_2$ alkyl; wherein:

the $C_1$-$C_2$ alkyl of $R^1$ is optionally substituted with 1 to 3 halogen.

23. The compound, tautomer, deuterated derivative, or pharmaceutically acceptable salt according to claim 1, wherein $R^2$, for each occurrence, is independently selected from Cl and —$CF_3$.

24. The compound, tautomer, deuterated derivative, or pharmaceutically acceptable salt according to claim 1, wherein k is an integer selected from 0, 1, and 2.

25. The compound, tautomer, deuterated derivative, or pharmaceutically acceptable salt according to claim 1, wherein m is an integer selected from 1 and 2.

26. The compound, tautomer, deuterated derivative, or pharmaceutically acceptable salt according to claim 1, wherein n is 0.

27. The compound, tautomer, deuterated derivative, or pharmaceutically acceptable salt according to claim 1, wherein the compound is selected from:

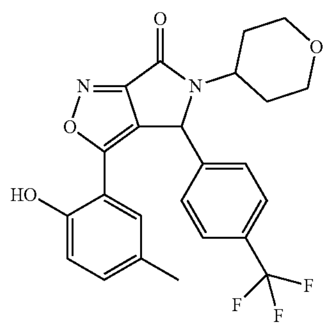

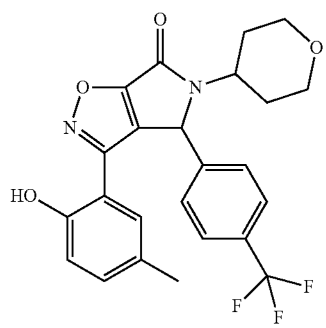

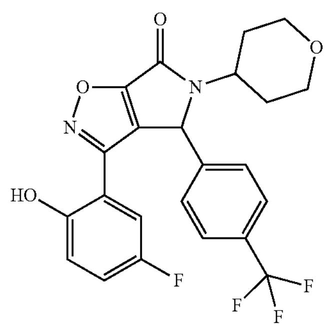

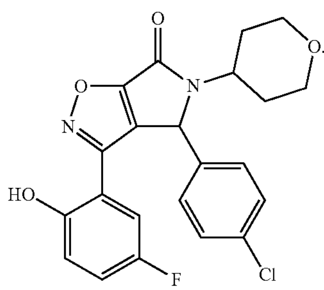

28. A pharmaceutical composition comprising a compound, tautomer, deuterated derivative, or pharmaceutically acceptable salt according to claim 1 and at least one pharmaceutically acceptable carrier.

29. A method of treating a disease, a disorder, or a condition mediated by the signaling of formyl peptide receptor 1 (FPR1) in a subject, comprising administering a therapeutically effective amount of a compound, tautomer, deuterated derivative, or pharmaceutically acceptable salt according to claim 1.

30. The method according to claim 29, wherein the disease, the disorder, or the condition is related to the CNS and is selected from stroke, dementia, Alzheimer's disease, Parkinson's disease, Picks disease, fronto-temporal dementia, vascular dementia, normal pressure hydrocephalus, epilepsy, seizure disorder, amyotrophic lateral sclerosis (ALS), spinal motor atrophies, Tay-Sach's, Sandoff disease, familial spastic paraplegia, spinocerebellar ataxia (SCA), Friedrich's ataxia, Wilson's disease, Menke's Sx, cerebral autosomal dominant arteriopathy with subcortical infarcts (CADASIL); spinal muscular atrophy, muscular dystrophies, Charcot Marie Tooth diseases, neurofibromatosis, von-Hippel Lindau, Fragile X, spastic paraplesia, tuberous sclerosis, Wardenburg syndrome, dystonias, benign essential tremor, tardive dystonia, tardive dyskinesia, Tourette's syndrome, ataxic syndromes, Shy Drager, Olivopontoicerebellar degeneration, striatonigral degenration, Gullian Barre syndrome, causalgia, complex regional pain syndrome types I and II, diabetic neuropathy, and alcoholic neuropathy, trigeminal neuropathy, trigeminal neuralgia, Menier's syndrome, glossopharangela neuralgia, dysphagia, dysphonia, cranial nerve palsies, myelopethies, traumatic brain injury, traumatic spinal injury, radiation brain injury, multiple sclerosis, post-menengitis syndrome, prion diseases, myelities, radiculitis, diabetes associated with dysproteinemias, transthyretin-induced neuropathies, neuropathy associated with HIV, neuropathy associated with Lyme disease, neuropathy associated with herpes zoster, carpal tunnel syndrome, tarsal tunnel syndrome, amyloid-induced neuropathies, leprous neuropathy, Bell's palsy, compression neuropathies, sarcoidosis-induced neuropathy, polyneuritis cranialis, heavy metal induced neuropathy, transition metal-induced neuropathy, drug-induced neuropathy, axonic brain damage, encephalopathies, chronic fatigue syndrome, and a malignant glioma.

31. The method according to claim 29, wherein the disease, the disorder, or the condition is stroke, wherein the stroke is selected from thrombotic stroke, embolic stroke, thromboembolic stroke, hemorrhagic stroke, venoconstrictive stroke, and venous stroke.

32. The method according to claim 29, wherein the disease, the disorder, or the condition is traumatic brain injury.

33. The method according to claim 29, wherein the disease, the disorder, or the condition is a malignant glioma.

34. The method according to claim 33, wherein the malignant glioma is selected from glioblastoma, anaplastic astrocytoma, anaplastic oligodendroglioma, anaplastic oligoastrocytoma, anaplastic ependymoma, and anaplastic ganglioglioma.

35. The method according to claim 34, wherein the malignant glioma is glioblastoma.

* * * * *